(12) United States Patent
Boudreault et al.

(10) Patent No.: US 9,033,992 B2
(45) Date of Patent: May 19, 2015

(54) METHODS AND APPARATUS FOR JOINT DISTRACTION

(75) Inventors: David Boudreault, Palo Alto, CA (US); Vivek Shenoy, Redwood City, CA (US); Hanson S. Gifford, Woodside, CA (US); Mark Deem, Mountain View, CA (US); Michael Hendricksen, Redwood City, CA (US); Doug Sutton, Pacifica, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 718 days.

(21) Appl. No.: 12/483,446

(22) Filed: Jun. 12, 2009

(65) Prior Publication Data

US 2009/0312807 A1  Dec. 17, 2009

Related U.S. Application Data

(60) Provisional application No. 61/061,457, filed on Jun. 13, 2008, provisional application No. 61/164,604, filed on Mar. 30, 2009.

(51) Int. Cl.
*A61B 17/58* (2006.01)
*A61B 17/60* (2006.01)
(Continued)

(52) U.S. Cl.
CPC ........... *A61B 17/025* (2013.01); *A61B 17/3421* (2013.01); *A61B 2017/00115* (2013.01); *A61B 2017/00557* (2013.01); *A61B 2017/0212* (2013.01); *A61B 2017/0275* (2013.01); *A61B 2017/3488* (2013.01); *A61M 25/0068* (2013.01); *A61M 25/008* (2013.01); *A61M 25/0102* (2013.01); *A61M 25/0147* (2013.01);
(Continued)

(58) Field of Classification Search
USPC ....................................... 606/57, 282, 90, 105
See application file for complete search history.

(56) References Cited

U.S. PATENT DOCUMENTS 3,840,014 A  10/1974  Ling et al.
3,875,595 A   4/1975  Froning
(Continued)

FOREIGN PATENT DOCUMENTS

DE  25 01 080  7/1976
EP  0 507 645  10/1992
(Continued)

OTHER PUBLICATIONS

International Search Report and Written Opinion of PCT Application No. PCT/US2009/047263, mailed Aug. 11, 2009, 20 pages total.
(Continued)

*Primary Examiner* — David Bates
*Assistant Examiner* — Samuel Hanna
(74) *Attorney, Agent, or Firm* — Pandiscio & Pandiscio

(57) ABSTRACT

A method of treating a patient's joint having opposing joint surfaces includes providing an elongate member having a proximal end, a distal end and an expandable member near the distal end. The expandable member is positioned in the joint between the joint surfaces and expanded so as to separate the joint surfaces away from one another into a distracted position. The joint is manipulated while in the distracted position so that the joint is distracted and in flexion. A diagnostic or therapeutic procedure is then performed on the joint while maintaining the joint in the flexed and distracted position.

21 Claims, 43 Drawing Sheets

(51) Int. Cl.

| | | |
|---|---|---|
| *A61F 2/00* | (2006.01) | |
| *A61B 17/02* | (2006.01) | |
| *A61B 17/34* | (2006.01) | |
| *A61M 25/10* | (2013.01) | |
| *A61B 1/317* | (2006.01) | |
| *A61F 5/01* | (2006.01) | |
| *A61B 17/00* | (2006.01) | |
| *A61M 25/00* | (2006.01) | |
| *A61M 25/01* | (2006.01) | |

(52) U.S. Cl.
CPC ....... *A61M25/1002* (2013.01); *A61M 25/1027* (2013.01); *A61M 2025/0063* (2013.01); *A61M 2025/0081* (2013.01); *A61M 2025/0163* (2013.01); *A61M 2025/1068* (2013.01); *A61M 2025/1072* (2013.01); *A61M 2025/1081* (2013.01); *A61M 2025/1086* (2013.01); *A61M 2025/1088* (2013.01); *A61B 1/317* (2013.01); *A61F 5/0193* (2013.01)

(56) References Cited

U.S. PATENT DOCUMENTS

| | | | |
|---|---|---|---|
| 4,467,479 A | | 8/1984 | Brody |
| 4,669,106 A | | 5/1987 | Ammerman |
| 4,772,266 A | | 9/1988 | Groshong |
| 4,874,375 A | | 10/1989 | Ellison |
| 4,928,670 A | * | 5/1990 | DeLorenzo ............... 602/26 |
| 4,968,316 A | | 11/1990 | Hergenroeder |
| 4,983,165 A | | 1/1991 | Loilerman |
| 4,995,875 A | | 2/1991 | Coes |
| 5,019,042 A | | 5/1991 | Sahota |
| 5,071,410 A | | 12/1991 | Pazell |
| 5,171,297 A | | 12/1992 | Barlow et al. |
| 5,176,683 A | | 1/1993 | Kimsey et al. |
| 5,213,112 A | * | 5/1993 | Niwa et al. ............... 600/587 |
| 5,234,455 A | | 8/1993 | Mulhollan |
| 5,290,220 A | | 3/1994 | Guhl |
| 5,342,386 A | | 8/1994 | Trotta |
| 5,344,459 A | | 9/1994 | Swartz |
| 5,411,475 A | | 5/1995 | Atala et al. |
| 5,411,517 A | | 5/1995 | Guignard |
| 5,704,372 A | | 1/1998 | Moll et al. |
| 5,725,545 A | | 3/1998 | Bircoll |
| 5,738,629 A | | 4/1998 | Moll et al. |
| 5,803,902 A | | 9/1998 | Sienkiewicz et al. |
| 5,817,123 A | | 10/1998 | Kieturakis et al. |
| 5,820,595 A | | 10/1998 | Parodi |
| 5,827,289 A | | 10/1998 | Reiley et al. |
| 5,827,318 A | | 10/1998 | Bonutti |
| 5,888,220 A | | 3/1999 | Felt et al. |
| 6,017,305 A | | 1/2000 | Bonutti |
| 6,123,718 A | | 9/2000 | Tu et al. |
| 6,171,236 B1 | | 1/2001 | Bonutti |
| 6,187,023 B1 | | 2/2001 | Bonutti |
| 6,217,548 B1 | | 4/2001 | Tsugita et al. |
| 6,468,289 B1 | | 10/2002 | Bonutti |
| 6,482,209 B1 | | 11/2002 | Engh et al. |
| 6,575,979 B1 | | 6/2003 | Cragg |
| 6,616,673 B1 | | 9/2003 | Stone et al. |
| 6,620,181 B1 | | 9/2003 | Bonutti |
| 6,855,149 B2 | | 2/2005 | Dye |
| 6,859,661 B2 | | 2/2005 | Tuke |
| 6,860,892 B2 | | 3/2005 | Tanaka et al. |
| 7,166,121 B2 | | 1/2007 | Reiley et al. |
| 7,189,229 B2 | | 3/2007 | Lopath et al. |
| 7,201,756 B2 | | 4/2007 | Ross et al. |
| 7,216,385 B2 | | 5/2007 | Hill |
| 7,217,273 B2 | | 5/2007 | Bonutti |
| 7,226,462 B2 | | 6/2007 | Tanaka et al. |
| 7,241,303 B2 | | 7/2007 | Reiss et al. |
| 7,300,448 B2 | | 11/2007 | Criscuolo et al. |
| 7,488,337 B2 | | 2/2009 | Saab et al. |
| 8,491,567 B2 | | 7/2013 | Magnin et al. |
| 2001/0001128 A1 | | 5/2001 | Holman et al. |
| 2001/0001315 A1 | | 5/2001 | Bates et al. |
| 2002/0177866 A1 | | 11/2002 | Weikel et al. |
| 2003/0004460 A1 | | 1/2003 | Bedell |
| 2003/0033017 A1 | * | 2/2003 | Lotz et al. ................. 623/17.16 |
| 2003/0220698 A1 | * | 11/2003 | Mears et al. ............... 623/22.4 |
| 2004/0059290 A1 | | 3/2004 | Palasis |
| 2004/0098015 A1 | | 5/2004 | Weikel et al. |
| 2004/0106861 A1 | * | 6/2004 | Leitner ..................... 600/407 |
| 2004/0116848 A1 | | 6/2004 | Gardeski et al. |
| 2004/0138754 A1 | | 7/2004 | Lang et al. |
| 2004/0236342 A1 | * | 11/2004 | Ferree et al. .............. 606/102 |
| 2004/0249360 A1 | | 12/2004 | Spehalski |
| 2005/0267482 A1 | | 12/2005 | Hyde, Jr. |
| 2006/0015171 A1 | | 1/2006 | Armstrong |
| 2006/0184246 A1 | | 8/2006 | Zwirkoski |
| 2006/0259063 A1 | | 11/2006 | Bates et al. |
| 2006/0293685 A1 | * | 12/2006 | Stone et al. ............... 606/90 |
| 2006/0293750 A1 | * | 12/2006 | Sherman et al. .......... 623/17.12 |
| 2007/0173946 A1 | | 7/2007 | Bonutti |
| 2007/0213759 A1 | | 9/2007 | Osborne et al. |
| 2007/0219561 A1 | * | 9/2007 | Lavallee et al. ........... 606/90 |
| 2007/0255394 A1 | | 11/2007 | Ryan |
| 2007/0265635 A1 | * | 11/2007 | Torrie et al. ............... 606/105 |
| 2007/0288095 A1 | | 12/2007 | Wirtel et al. |
| 2008/0019004 A1 | | 1/2008 | Hansen |
| 2008/0045967 A1 | | 2/2008 | Lubinus et al. |
| 2008/0109004 A1 | | 5/2008 | Da Rold et al. |
| 2009/0112214 A1 | * | 4/2009 | Philippon et al. ......... 606/90 |
| 2009/0299282 A1 | | 12/2009 | Lau et al. |
| 2009/0312807 A1 | | 12/2009 | Boudreault et al. |
| 2010/0312179 A1 | | 12/2010 | Nikolchev et al. |

FOREIGN PATENT DOCUMENTS

| | | |
|---|---|---|
| FR | 1 061 009 | 4/1954 |
| FR | 2 734 146 | 11/1996 |
| WO | WO 92/22259 | 12/1992 |
| WO | WO 97/27897 | 8/1997 |
| WO | WO 99/59669 | 11/1999 |
| WO | WO 00/23009 | 4/2000 |
| WO | WO 01/45601 | 6/2001 |
| WO | WO 2005/048812 | 6/2005 |
| WO | WO 2007/080454 A2 | 7/2007 |
| WO | WO 2007/092841 | 8/2007 |
| WO | WO 2009/042429 | 4/2009 |
| WO | WO 2010/097724 | 2/2010 |
| WO | WO 2010/107949 | 9/2010 |
| WO | WO 2012/064786 | 5/2012 |

OTHER PUBLICATIONS

GB Combined Search and Examination Report of Application No. GB0910155.1, dated Jul. 21, 2009, 4 pages total.

Aydin et al., "A New Noninvasive Controlled Intra-articular Ankle Distraction Technique on a Cadaver Model," Arthroscopy: The Journal of Arthroscopic and Related Surgery, Aug. 2006. 22(8): 905.e-905.e3.

Burman, "Arthroscopy or the direct visualization of joints: an experimental cadaver study," Journal of Bone and Joint Surgery, Oct. 1931;13(4):669-695; retrieved from the Internet: <<http://www.ejbjs.org/cgi/reprint/13/4/669>>.

Dienst, Chapter 11: Hip arthroscopy without traction, Byrd, ed., *Operative Hip Arthroscopy*, 2nd Edition, Byrd, ed., Springer New York, 2005, pp. 170 and 174.

Dienst et al., "Hip arthroscopy without traction: In vivo anatomy of the peripheral hip joint cavity," Arthroscopy, 2001; 17(9): 924-931.

Sartoretti et al., "Angioplasty Balloon Catheters Used for Distraction of the Ankle Joint," Arthroscopy: The Journal of Arthroscopic and Related Surgery, Feb. 1996; 12(1): 82-86.

Shetty, "Hip arthroscopy: current concepts and review of literature," Br J Sports Med, 2007; 41(2): 64-68; discussion 68; retrieved from the Internet: <<http://bjsm.bmj.com/cgi/reprint/41/2/64>>.

Tan et al., "Contribution of acetabular labrum to articulating surface area and femoral head coverage in adult hip joints: an anatomic study in cadavera," Am J Orthop, 2001; 30(11): 809-812.

(56) References Cited

OTHER PUBLICATIONS

U.S. Appl. No. 61/061,457, filed Jun. 13, 2008; first named inventor: Vivek Shenoy.
U.S. Appl. No. 61/164,604, filed Mar. 30, 2009; first named inventor: Vivek Shenoy.
Byrd, Operative Hip Arthroscopy, 2005, 146-147.
Ganz et al., Surgical dislocation of the adult hip, The Journal of Bone and Joint Surgery, Nov. 2001, vol. 83-B, No. 8, 1119-1124.
Dienst et al., Effects of Traction, Distension, and Joint Position on Distraction of the Hip Joint: An Experimental Study in Cadavers, Arthroscopy: The Journal of Arthroscopic and Related Surgery, Oct. 2002, vol. 18, No. 8, 865-871.

* cited by examiner

SEC. A-A

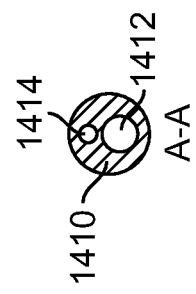
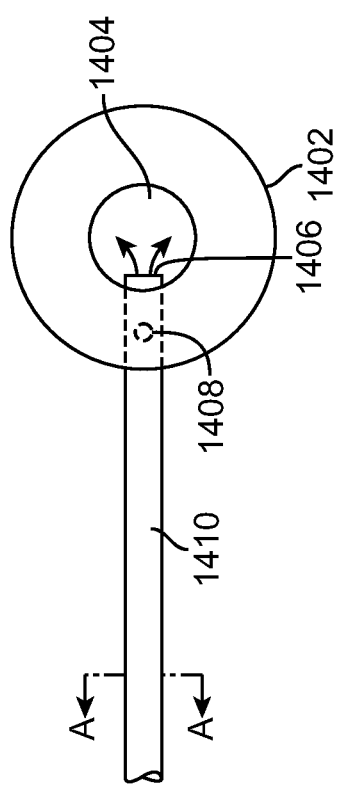
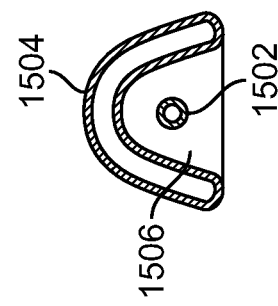
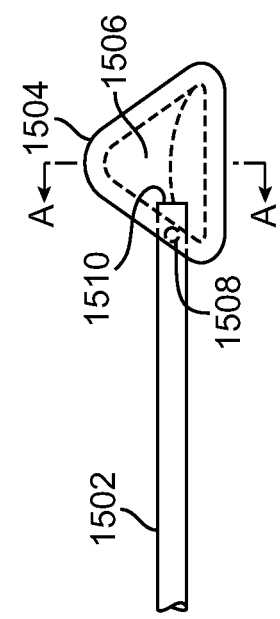

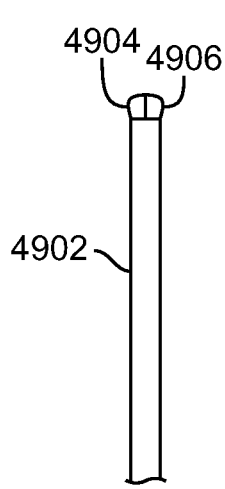
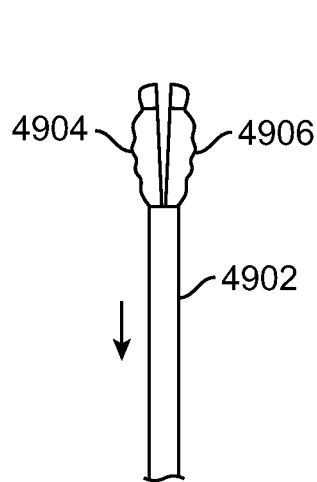
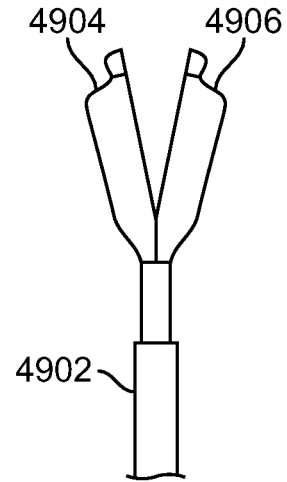
FIG. 27A         FIG. 27B         FIG. 27C
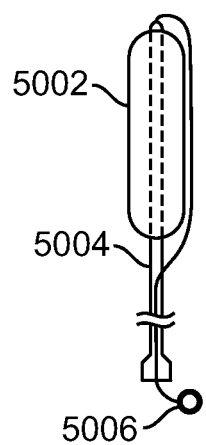
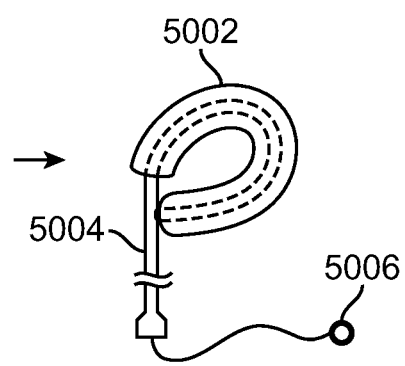
FIG. 28A         FIG. 28B

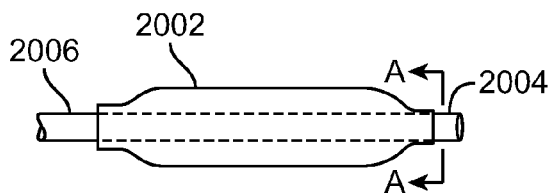 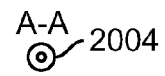
FIG. 38A   FIG. 38B
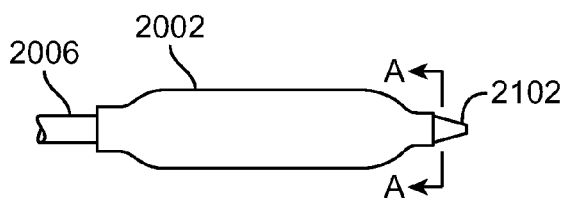 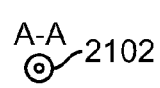 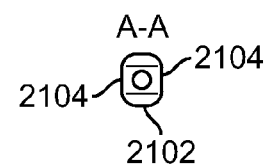
FIG. 39A   FIG. 39B   FIG. 39C
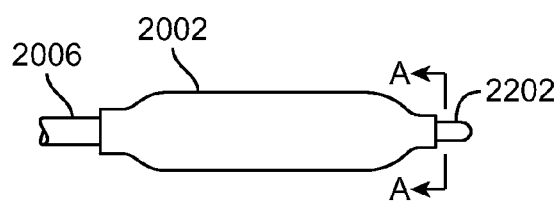 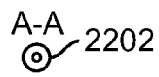
FIG. 40A   FIG. 40B

METHODS AND APPARATUS FOR JOINT DISTRACTION

CROSS-REFERENCES TO RELATED APPLICATIONS

The present application is a non-provisional of, and claims the benefit of priority under 35 U.S.C. §119(e) of U.S. Provisional Application No. 61/061,457 filed Jun. 13, 2008, the entire contents of which are incorporated herein by reference. The present application is also a non-provisional of, and claims the benefit of priority under 35 U.S.C. §119(e) of U.S. Provisional Application No. 61/164,604 filed Mar. 30, 2009, the entire contents of which are incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of the Invention

The present disclosure relates to medical devices and methods, and more specifically to methods and devices used to distract joints including, but not limited to the hip, shoulder, ankle, and wrist joint. Joint distraction enables introduction of therapeutic or diagnostic instruments into the joint space so that various medical procedures may be performed on the joint.

Arthroscopy is a minimally invasive surgical procedure used in the examination and treatment of joint disease or damage. While arthroscopic treatment of the knee and shoulder joints is common today, fewer arthroscopic procedures are performed in other joints such as the hip, ankle and wrist joint due to challenges associated with accessing the joint space.

In the case of the hip joint, it is the deepest and largest joint in the body. The hip joint is formed between the head of the femur and the acetabulum and is a very difficult joint to separate. This is due in large part to a blanket of ligaments and tendons that cover the joint, forming a tight sealed capsule. Additionally the acetabular labrum, a fibrocartilaginous lip, surrounds the head of the femur, deepening the joint pocket and increasing the surface area of contact. The labrum divides the hip joint into two compartments within the joint capsule: central and peripheral. The central compartment is within the confines of the labrum and contains the majority of the articular cartilage and the ligamentum teres, a ligament attached to a depression in the acetabulum (the acetabular notch or fossa) and a depression on the femoral head (the fovea of the head). The peripheral compartment is the space outside the labrum and within the capsule.

In order to provide access to a joint space for a diagnostic or therapeutic procedure, the joint often must be distracted. Distraction is the term used to define a combination of traction and distention used to separate the joint, which in the case of a hip joint, allows the surgeon to access the central compartment. This is typically accomplished by positioning a patient on a distraction table and applying forces of 50-70 pounds to the patient's foot while the pelvis is constrained by a post positioned against the perineum. The traction is maintained as long as access to the central compartment is needed.

This external method of joint distraction is not without challenges and can result in complications. The most common complications are the transient neuropraxias of the sciatic, lateral femoral cutaneous and pudendal nerves. Additionally, pressure applied to the foot and perineum during distraction can result in pressure necrosis of the skin and underlying tissue, as well as vaginal and anal tears. Problems with lacerations to the lateral femoral cutaneous nerve can also occur, which leaves permanent numbness to the anterior thigh. Additionally, once traction is applied to the joint, it is difficult to further manipulate the joint to alter joint position or provide increased access to the joint space since distraction tables often have rigid arms or fixtures that must be locked into position. Further, because traction tables rely on the application of tensile force to the foot, the knee cannot be bent while traction is maintained. While some traction tables permit some degree of flexion, abduction, or adduction while traction is applied, because the knee must be straight, the degree of such manipulation is substantially limited. Flexion in particular is limited to less than 20° due to the potential risk of sciatic nerve damage.

Moreover, when traction is applied to a joint, tension in adjacent tissue often increases, further increasing difficulty of accessing the joint space. In the case of the hip joint, application of traction results in increased tension in the ligaments and tendons of the capsule which further inhibits introduction and manipulation of arthroscopic instruments in the joint space. It would therefore be desirable to provide devices and method that overcome some or all of these challenges.

Arthroscopy in the ankle and wrist also require distraction for access into certain joint areas. However, unlike the hip, the distraction forces aren't high, ranging from 10-30 lbs. Nevertheless, distraction of the ankle and wrist share similar challenges to treatment as the hip joint.

Balloon catheter technology has been widely adopted in cardiovascular applications and is now also being used in other areas including orthopedic applications such as kyphoplasty and otolaryngology applications like sinuplasty. The use of balloons for internal distraction of a joint has been proposed. For example, Aydin et al. has reported the use of a kyphoplasty balloon to distract an ankle joint while Sartoeretti has disclosed the use of angioplasty balloons for ankle distraction. U.S. Pat. No. 6,017,305 to Bonutti discloses the use of an inflatable bladder to retract bones and U.S. Pat. No. 6,616,673 to Stone discloses a method of separating a hip joint with a device having several expandable spheroid regions. While some of these devices and methods appear to be promising, they are not without challenges. For example, using existing balloons which are often small sized may require excessive pressures to achieve the necessary distraction force and in the case of the hip joint, existing balloons may not distract the joint surfaces enough (e.g. at least about 10 to 12 mm) to allow access for other surgical instruments. Other devices may be inflatable to an appropriate size but they may also occupy too much of the joint space limiting access for instruments. Further because these devices may engage a wide area of the joint, they may also limit joint manipulation. Moreover, some the disclosed devices also still require external distraction in order to initially place the device into the joint due to their large unexpanded profile.

In view of these challenges, it would be desirable to provide improved devices and methods for distracting joints such as the hip, ankle, shoulder and wrist joint, as well as other joints. Such methods and devices preferably would be cost effective, easy to manufacture and simple to use. Furthermore, such methods preferably have lower complication rates than existing distraction methods and devices and also provide easy and wide access to the joint space without requiring external traction. In addition to distracting the joint, such methods and devices preferably allow easy introduction of other diagnostic or therapeutic instruments into the joint space. Moreover, the methods and devices preferably also allow the joint to be manipulated while in the distracted position in order to allow increased access to the joint or access to other regions of the joint space. Some or all of these objectives will be met by the devices and methods disclosed herein.

2. Description of the Background Art

Scientific publications of interest in connection with the present invention include Burman, M. S., *Arthroscopy or the direct visualization of joints: an experimental cadaver study.* 1931. Clin Orthop Relat Res, 2001(390): p. 5-9; Tan, V., et al., *Contribution of acetabular labrum to articulating surface area and femoral head coverage in adult hip joints: an anatomic study in cadavera.* Am J Orthop, 2001. 30(11): p. 809-12; Dienst, M., et al., *Hip arthroscopy without traction: In vivo anatomy of the peripheral hip joint cavity.* Arthroscopy, 2001. 17(9): p. 924-31; Shetty, V. D. and R. N. Villar, *Hip arthroscopy: current concepts and review of literature.* Br J Sports Med, 2007. 41(2): p. 64-8; discussion 68; Sartoretti, C., et al., *Angioplasty Balloon Catheters Used for Distraction of the Ankle Joint.* Arthroscopy: The Journal of Arthroscopic and Related Surgery, 1996. 12(1), February: p. 82-86; and Aydin, A., et al., *A New Noninvasive Controlled Intra-articular Ankle Distraction Technique on a Cadaver Model.* Arthroscopy: The Journal of Arthroscopic and Related Surgery, 2006. 22(8), August: p. 905.e-905.e3;

Patents of interest in connection with the present invention include EP 507645 and U.S. Pat. Nos. 7,226,462; 6,616,673; 6,017,305; 5,290,220; and 4,467,479. Patent publications of interest include U.S. Patent Publication Nos. 2009/0112214; and 2006/0293685 and PCT Publication Nos. WO 2007/080454; and WO 00/23009.

BRIEF SUMMARY OF THE INVENTION

The present invention generally relates to medical methods and devices, and more specifically to methods and devices used to distract joints including, but not limited to the hip, ankle, shoulder, knee and wrist joints. Joint distraction enables introduction of therapeutic or diagnostic instruments into the joint space so that other medical procedures may be performed on the joint.

In a first aspect of the present invention, a method of treating a patient's joint having opposing joint surfaces comprises providing an elongate member having a proximal end, a distal end and an expandable member near the distal end. The expandable member is positioned in the joint between the joint surfaces and expanding the expandable member separates the joint surfaces away from one another into a distracted position. While the joint surfaces remain in the distracted position, the joint is manipulated into a manipulated configuration in which the joint is in both flexion and distraction. A diagnostic or therapeutic procedure is performed on the joint while maintaining the joint in the manipulated configuration. In some embodiments, the expandable member may be positioned in the joint without applying external traction thereto.

Positioning may comprise advancing the expandable member over a guidewire or through a cannula into the joint which may be a hip joint. The hip joint has an acetabular fossa, and the step of positioning may comprise advancing the expandable member through a cannula extending into the joint capsule. The expandable member may remain in the fossa as it is expanded. The hip joint also has an acetabulum and a femoral head coupled together with a ligamentum teres, and the expandable member may be positioned posterior to the ligamentum teres. In some embodiments, a retention mechanism may be deployed from the cannula in order to anchor the cannula into the joint.

Expanding the expandable member may comprise inflating a balloon. The balloon may be inflated to a pressure not exceeding about 100 psi and the balloon may exert at least about 25 pounds of force against the joint surfaces. The expandable member may engage each joint surface within a contact area no more than about 800 square millimeters. Each joint surface has a total area, and the expandable member may engage each joint surface within a contact area no larger than about 50% of the total area and more preferably less than about 30% of the total area when the expandable member is expanded. The balloon has an outer surface with a radius of curvature when expanded and the radius of curvature may be about 8-18 mm. When the joint is a hip joint having a total joint surface area of the acetabulum outside the fossa, the balloon may contact one of the joint surfaces along a contact area, and preferably no more than about 50%, and more preferably less than about 30% of the total joint surface area is contacted by the balloon or expandable member when expanded. Expanding the expandable member may separate the joint surfaces at least about 10 mm away from one another. Also, expanding the expandable member may fluidly isolate a portion of the joint from the remainder of the joint. Balloon position may be adjusted within the joint in order to change the joint separation.

Manipulating the joint may further comprise one or more of flexion, extension, lateral rotation, medial rotation, abduction and adduction of the joint. The joint may be placed in up to about 20 degrees of flexion, up to about 30 to 80 degrees of abduction, and/or up to about 10 to 30 degrees of adduction. When the joint comprises a hip joint, a capsule surrounds the joint and manipulating the hip joint reduces tension in the joint capsule which makes it easier for a device to be inserted through the capsule and under the labrum. One or more instruments may be positioned through the relaxed portion of the joint capsule while the tension is reduced in order to perform a diagnostic or therapeutic procedure. Manipulation of the joint may be performed while the expandable member is expanded.

Performing the diagnostic or therapeutic procedure may comprise arthroscopically viewing the joint. The diagnostic or therapeutic procedure may also comprise one or more of labral repair or debridement, lavage, osteotomy, microfracture or chondral repair of the joint surfaces or tissue adjacent thereto. Tissue adjacent the joint may also be distended by infusion of fluid into the tissue, such as the hip joint capsule.

The joint may be a hip joint and the step of manipulating the joint may further comprise bending a knee ipsilateral to the hip joint. The hip joint may be maintained in the manipulated and distracted configuration with a brace that is releasably coupled with the patient's leg that is ipsilateral to the hip joint. After the expandable member has been expanded, the method may further comprise contracting the expandable member and actively reducing profile of the contracted expandable member. A stylet may be positioned in a lumen in the elongate member during the advancing step. Also a portion of the elongate member may be actively deflected into a curved configuration. Expanding the expandable member may comprise inflating a balloon with an inflation medium that is stored in a reservoir of an inflation device. A switch on the inflation device may be actuated so as to deliver a predetermined volume of inflation medium from the reservoir to the balloon thereby expanding the expandable member which may be a balloon. In some embodiments the expandable member may be detachably coupled with the elongate member such that the elongate member may be detached from the expandable member while seated in the joint or fossa of the joint in an expanded configuration. Sometimes, a spacer may be inserted into the joint after expansion of the balloon or expandable member, or after the joint has been separated.

In another aspect of the present invention, a hip joint comprises an acetabulum, an acetabular fossa and a femoral head and a method of treating a patient's hip joint comprises providing an elongate member having a proximal end, a distal end and an expandable member near the distal end. The expandable member is advanced into the hip joint between the femoral head and the acetabulum and positioned into the acetabular fossa. The expandable member is expanded thereby separating the femoral head from the acetabulum while the expandable member remains in the acetabular fossa. A diagnostic or therapeutic procedure is then performed on the hip joint while the expandable member is expanded within the acetablular fossa.

The expandable member may have an axial length that is no more than about 1.3 times the diameter of the expandable member when expanded. A distal portion of the elongate member may be substantially more flexible than a proximal portion of the elongate member. The elongate member may comprise a distal tip that extends a distance no more than about 10 mm from a distal end of the expandable member.

The distal end may extend distally of the expandable member and the distal end may be slidably advanced through and beyond the acetabular fossa without traumatic engagement with tissue therein. The acetabulum has a curvature and a distal portion of the elongate member may have a curvature in an unbiased condition selected to follow the curvature of the acetabulum as the distal portion is advanced. Advancing may be performed without applying external traction.

Positioning the expandable member may comprise advancing the expandable member over a guidewire or through a cannula extending into the joint capsule. The acetabulum and the femoral head are coupled together by a ligamentum teres, and the expandable member may be positioned posterior to the ligamentum teres.

Expanding the expandable member may comprise inflating a balloon. The balloon may be inflated to a pressure not exceeding about 100 psi. The balloon may exert at least about 25 pounds of force against the femoral head and the acetabulum when inflated. The expandable member may engage the femoral head and the acetabulum within a contact area that is no more than about 800 square millimeters. The hip joint comprises a total joint surface area of the acetabulum outside the fossa and the balloon contacts the joint surface along a contact area no more than about 50%, and more preferably less than about 30% than total joint surface area when the balloon is expanded. Expanding the expandable member separates the femoral head and the acetabulum at least about 10 mm away from one another. Expanding the expandable member may also fluidly isolate a portion of the hip joint from the remainder of the hip joint.

Performing the diagnostic or therapeutic procedure may comprise arthroscopically viewing the hip joint. Viewing the joint may include viewing the acetabulum or the femoral head posterior to the expanded expandable member. Diagnostic or therapeutic procedures may comprise one or more of labral repair, debridement, flushing, smoothing, microfracture, or chondral repair of the femoral head, the acetabulum or adjacent tissue. The method may also include distending a capsule surrounding the hip joint before advancing the expandable member. Distension may be accomplished by infusing fluid into the capsule.

The hip joint may be manipulated while the femoral head and the acetabulum remain separated from one another so that the hip joint is in a manipulated and a distracted configuration. The hip joint may be in flexion while in the manipulated and distracted configuration. The therapeutic or diagnostic procedure may be performed while the hip is in the manipulated and distracted configuration.

In still another aspect of the present invention a hip joint has an acetabulum and an acetabular fossa and an apparatus for distracting a hip joint comprises an elongate flexible member having a proximal end and a distal end and an expandable member coupled with the elongate member near the distal end. The expandable member is expandable from a collapsed configuration to an expanded configuration and the expandable member has a transverse dimension of at least about 10 mm in the expanded configuration and also has an expanded shape and expanded size selected so that the expandable member seats in the acetabular fossa.

The expandable member may be configured to apply a radial force of at least 50 pounds when expanded to a pressure of no more than 100 psi. The expandable member may be configured to engage a portion of the the total surface of the acetabulum outside of the fossa only within a contact surface, and the contact surface is no more than about 50%, and preferably less than about 30% of the total surface when the expandable member is in the expanded configuration. The joint surface is the total surface area of the acetabulum outside the fossa. The expanded size and the expanded shape may be selected so that the expandable member is biased into the fossa when expanded. The expandable member may have an outer surface with a radius of curvature of at least about 8 mm in the expanded configuration. The expandable member may have an axial length in the expanded configuration that is no more than about 1.5 times the width of the acetabular fossa. The expandable member may also have an axial length that is no more than about 0.8 to about 1.3 times the diameter of the expanded expandable member when expanded. The contact surface of the expandable member may be at least about 200 square millimeters and less than about 800 square millimeters. The flexible member may comprise at least one lumen extending between the proximal and distal ends.

The expandable member may comprise a balloon. Some of the possible shapes of the expandable member include generally, dome shaped, spherical, a flat inferior side with a semi-spherical superior side, or a central bulbous region with an annular region surrounding the bulbous region. The expandable member may comprise at least two expandable regions, with each region being expandable independently of the other. Other expandable member configurations include having a distal taper different than the proximal taper. The distal taper may be steeper than the proximal taper. The proximal taper may be in the range of about 10 to about 45 degrees and the distal taper may be in the range of about 30 to about 90 degrees. Sometimes the proximal and distal tapers are opposite and thus the distal taper may be in the range of about 10 to about 45 degrees and the proximal taper may be in the range of about 30 to about 90 degrees. The expandable member may comprise an invaginated end fixedly attached with the elongate member.

The expandable member may have a toroidal region and the elongate member may be coupled with a lateral portion of the toroidal region such that a longitudinal axis of the elongate member is substantially perpendicular to a central axis of the toroid. The toroidal region may have an open central region and the elongate member may comprise one or more apertures near the distal end opening into the central region to allow egress of fluid or tools therefrom into the center of the toroid. The expandable member may comprise surface features that are adapted to facilitate retention of the expandable member in the acetabular fossa. Some of these surface features may include projections, bumps, ridges, and sticky regions. The expandable member may also comprise a lubricious coating adapted to facilitate withdrawal of the expandable member through a sheath. The expandable member may further comprise a puncture resistant layer of material.

The apparatus may further comprise means for collapsing the balloon. The means for collapsing the balloon may comprise a shaft rotationally engaged with the expandable member such that the shaft is adapted to rotate and collapse the expandable member. The means for collapsing the balloon may also comprise a linearly actuatable shaft coupled with the expandable member such that the shaft is adapted to stretch the expandable member into a flattened configuration. The expandable member may be expanded with a fluid having a refractive index, and the expandable member may be composed of a material having a refractive index substantially the same as the refractive index of the fluid. The expandable member may also comprise a coating adapted to enhance translucency or reduce reflection of light. The apparatus may further comprise a fiber optic filament disposed in the elongate member for transmitting light from a light source.

The elongate member may comprise a distal tip adapted to be passed into and through the hip joint without causing trauma to the joint or tissue adjacent thereto. The distal tip may have a curvature with a radius no larger than a curvature of the acetabulum so that the distal tip is biased away from the acetabular surfaces as the elongate member is passed into and through the hip joint. The distal tip may extend no more than about 10 mm from a distal end of the expandable member. The distal tip may comprise various shapes including substantially straight, conical, curved, J-shaped, and pigtail shaped. The distal tip may also comprise a tapered region. The tapered region may be on two opposing sides so as to be more flexible about one transverse axis than about a second transverse axis. The distal tip may be resilient and biased to return to a predefined unbiased shape.

The elongate member may comprise a curved region in a distal portion of the elongate member and the curved region may have a radius within ±20% of the radius of the acetabulum. The apparatus may further comprise a stylet removably disposed in a lumen of the elongate member and that is adapted to straighten the elongate member during advancement of the elongate member into the hip joint. The stylet may be removably disposed in a lumen of the elongate member in order to increase columnar strength of the elongate member. The stylet may be disposed in a lumen of the elongate member and it may have a curved portion that is adapted to form a corresponding curve in the elongate member. The stylet may comprise a plurality of parallel slots transverse to the longitudinal axis of the stylet in order to allow bending of the stylet. The parallel slots may be disposed only on a first side of the stylet such that the stylet bends more easily in a first direction than in a second direction. The stylet may also have a cross-sectional width that is greater than its cross-sectional height so that the stylet bends more easily in a first direction than in a second direction. The elongate member may also comprise a distal nosecone and a stylet disposed in a lumen of the elongate member. The nosecone often is conical, but one of skill in the art will appreciate that other configurations are possible and may be non-conical. The stylet may be keyed to the nosecone such that rotation of the stylet rotates the nosecone. Rotation of the stylet may rotate a distal end of the expandable member relative to a proximal end of the expandable member.

The elongate member may comprise a guidewire lumen. The elongate member may comprise a distal guidewire port and a proximal guidewire port, each may be sized to allow passage of a guidewire slidably therethrough and the proximal guidewire port may be disposed proximal to the expandable member and closer to the distal end of the elongate member than the proximal end. The apparatus may also comprise a guidewire at least partially disposed in the elongate member and a stopping element may be coupled with the guidewire. The stopping element may be adapted to constrain advancement of the guidewire into the elongate member.

The elongate member may comprise a cross-sectional geometry selected to allow bending around one transverse axis of the elongate member more easily than around other transverse axes. This geometry may include an oval, racetrack, and rectangular shape. The elongate member may have a width along a first transverse axis substantially greater than a height of the elongate member taken along a second transverse axis orthogonal to the first axis. The elongate member may comprise one or more lumens, and the elongate member may be biased to collapse to a flattened configuration when the one or more lumens are evacuated.

The apparatus may further comprise a pullwire disposed in a lumen of the elongate member and operably coupled with a distal portion of the elongate member such that actuation of the pullwire forms a curve in the distal portion of the elongate member. The elongate member may comprise a distal tip extending distally of the expandable member and the curve is formed only in the distal tip. The apparatus may also have an actuator mechanism near the proximal end of the elongate member that is operably coupled with the pullwire. The apparatus may have a shield positionable over at least a portion of the expandable member and the shield may be able to prevent puncture of the expandable member.

In another aspect of the present invention, a medical apparatus comprises an inflatable member positionable in a body cavity and having an interior. An elongate flexible shaft has a proximal end, a distal end, an inflation lumen extending therebetween, and a cross-sectional height. The distal end of the shaft is coupled with the inflatable member and the inflation lumen is in fluid communication with the interior of the inflatable member. The shaft comprises a collapsed profile and an expanded profile and the cross-sectional height in the collapsed profile is substantially less than the cross-sectional height in the expanded profile. Also, the shaft is biased to remain in the collapsed profile.

The cross-sectional height in the expanded profile may be at least about twice the cross-sectional height in the collapsed profile. A stylet may be slidably and removably disposed in a stylet lumen of the shaft. The shaft may have a first column strength when the stylet is removed from the stylet lumen and a second column strength when the stylet is disposed in the stylet lumen. The second column strength may be substantially greater than the first column strength. Passage of an inflation fluid through the inflation lumen to the interior of the inflatable member may expand the shaft from the collapsed profile to the expanded profile. The shaft comprises a cross-sectional width, and in the collapsed profile the cross-sectional width may be substantially greater than the cross-sectional width in the expanded profile. The cross-sectional width may be greater than the cross-sectional height in both the expanded and collapsed profiles. The shaft also comprises a longitudinal axis and an axis transverse thereto, and the shaft may be configured to bend about the transverse axis more easily than at least one other transverse axis.

The inflatable member has an inflated shape and inflated size selected so that when inflated within a hip joint, the inflatable member may seat in an acetabular fossa of the hip joint. When inflated to a pressure less than about 100 psi, the inflatable member may be adapted to apply a pressure of at least 50 pounds. The inflatable member has a contact surface for engaging the surface of the acetabulum outside the fossa, and no more than 50%, and more preferably less than about 30% of the acetabular surface outside the fossa is contacted when the when the inflatable member is inflated.

In still another aspect of the present invention, a medical apparatus comprises an inflatable member positionable in a body cavity and having an interior. An elongate flexible shaft has a proximal end, a distal end and an inflation lumen extending therebetween. The distal end of the shaft is coupled with the inflatable member and the inflation lumen is in fluid communication with the interior of the inflatable member. The shaft has a longitudinal axis and a first axis transverse thereto and the shaft bends substantially more easily about the first transverse axis than about at least one other transverse axis.

The shaft has a cross-sectional height and a cross-sectional width. The cross-sectional height may be substantially less than the cross-sectional width. The cross-sectional shape may include rectangular, oval, and racetrack shapes. The inflatable member has an inflated shape and an inflated size selected so that when inflated within a hip joint, the inflatable member may seat in an acetabular fossa of the hip joint. When inflated to a pressure less than about 100 psi, the inflatable member may be adapted to apply a pressure of at least 50 pounds. The inflatable member has a contact surface for engaging the acetabulum of the hip joint and no more than 50%, and preferably less than 30% of the total surface of the acetabulum outside the fossa is contacted by the inflatable member when inflated.

In another aspect of the present invention, a system for distracting a joint surrounded by a joint capsule comprises an inflatable member having an interior and an elongate flexible shaft coupled with the inflatable member. The shaft has an inflation lumen in fluid communication with the interior of the inflatable member and an inflation unit is coupled with the shaft. The inflation unit comprises an inflation fluid reservoir fluidly coupled with the inflation lumen, a displacement mechanism for delivering fluid from the reservoir into the inflation lumen, and a controller. The controller has a switch and actuation of the switch causes movement of the displacement mechanism thereby delivering a predetermined volume of inflation fluid to the interior.

The inflatable member has an inflated volume that may be selected to distract the joint by a desired distance and the predetermined volume may be equal to the inflated volume. Actuation of the switch causes movement of the displacement mechanism thereby evacuating inflation fluid from the interior. The displacement mechanism may comprise a motor and a power supply electrically coupled therewith. The switch may comprise an electronic switch. The predetermined volume may be at least 16 mL and the inflation unit may be adapted to deliver the predetermined volume at pressures up to 200 psi. The inflation fluid may comprise saline, contrast media or combinations thereof. The predetermined volume may be selected to incrementally or fully inflate the inflatable member in a single step. The system may also include a distraction sensor that is adapted to indicate the amount of joint distraction. The system may have a guidewire and the elongate flexible shaft is advanceable over the guidewire to the joint.

Sometimes the joint comprises a hip joint having an acetabular fossa and the inflatable member has an inflated shape and an inflated size selected so that when inflated, the inflatable member may seat in an acetabular fossa of the hip joint. When inflated to a pressure less than about 100 psi, the inflatable member is adapted to apply a pressure of at least 50 pounds. The inflatable member has a contact surface for engaging the acetabulum of the hip joint and no more than about 50%, and preferably less than 30% of the total acetabular surface outside the fossa is contacted by the inflatable member when inflated.

In another aspect of the present invention, a system for distracting a joint comprises an inflatable member having an interior and an elongate flexible shaft coupled with the inflatable member. The shaft has a guidewire lumen and an inflation lumen in fluid communication with the interior of the inflatable member. The system also includes an arthroscopic instrument adapted to diagnose or repair the joint.

The instrument may include one of a retractor, a cutter, a debrider, a suture anchor, and a grasper. The system may also include a guidewire that is at least partially disposed in the elongate shaft and a stopping element may be coupled with the guidewire. The stopping element constrains advancement of the guidewire into the guidewire lumen. The system may include a shield device positionable at least partially over the inflatable member. The shield may be adapted to prevent puncture of the inflatable member.

In yet another aspect of the present invention, a system for distracting a joint surrounded by a joint capsule comprises an elongated cannula having a central channel therethrough with a distal end positionable in the joint capsule and a retention mechanism for holding the cannula in the joint capsule. The system also includes a distraction device. The distraction device has an elongated shaft and an expandable balloon near the distal end of the shaft. The balloon is positionable through the central channel. The distraction device is configured to be inserted through the central channel and into the joint to hydraulically distract the joint.

The retention mechanism may be attached to the cannula. The retention mechanism may be coupled to a second shaft positionable through the central channel. The retention mechanism may comprise a radially expandable portion of the cannula or a plurality of resilient filaments that are biased to flare radially outward when unconstrained by the cannula. The retention mechanism may be configured to engage an inner or outer surface of the joint capsule. The retention mechanism may have an inner portion that is positionable within the joint capsule and an outer portion that is positionable outside the joint capsule. The cannula may comprise two halves that may be separated from one another.

These and other embodiments are described in further detail in the following description related to the appended drawing figures.

BRIEF DESCRIPTION OF THE DRAWINGS

FIGS. 22A-22B illustrate another exemplary embodiment of a distraction balloon.

FIGS. 23A-23B illustrate still another exemplary embodiment of a distraction balloon.

FIGS. 24, 25A-25B, 26A-26B, 27A-27C and 28A-28B show other exemplary embodiments of distraction balloons.

FIGS. 38A-38B illustrate an exemplary embodiment of a distraction balloon tip.

FIGS. 39A-39C illustrate another embodiment of a distraction balloon tip.

FIGS. 40A-40B illustrate yet another embodiment of a distraction balloon tip.

DETAILED DESCRIPTION OF THE INVENTION

The methods and devices disclosed in this specification will be discussed mainly in terms of exemplary embodiments involving the hip joint. One of skill in the art will of course appreciate that these methods and devices may be used on other joints including but not limited to the shoulder, ankle or wrist joint, and that disclosure of hip joint distraction is not intended to be limiting.

Figure 1:
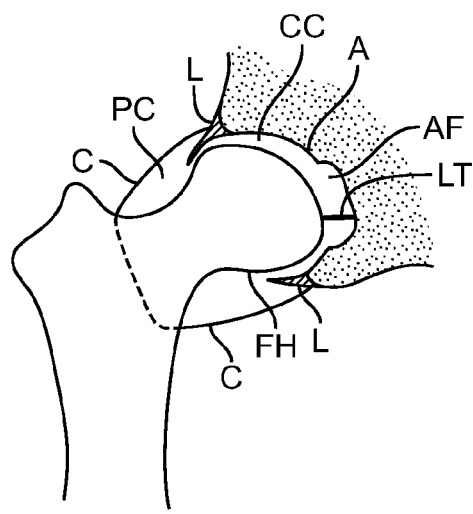
FIG. 1 illustrates the anatomy of a hip joint.

FIG. 1 illustrates the basic anatomy of a hip joint. In FIG. 1 the hip joint is formed between the head of the femur FH and the acetabulum A, a concave surface of the pelvis. The acetabular fossa AF is a recessed region in the acetabulum. A blanket of ligaments cover the joint forming a capsule C. Additionally the acetabular labrum, a fibrocartilaginous lip, surrounds the head of the femur, deepens the joint pocket and increases the surface area of contact. The labrum L divides the hip joint into two compartments within the joint capsule: a central compartment CC and a peripheral compartment PC. The central compartment CC is within the confines of the labrum L and contains the majority of the joint cartilage and the ligamentum teres LT, a ligament attached to a depression in the acetabulum (the acetabular notch or fossa) and a depression on the femoral head (the fovea of the head). The peripheral compartment PC is everything outside the labrum. The central compartment CC is not visible until the joint has been distracted.

Figure 2:
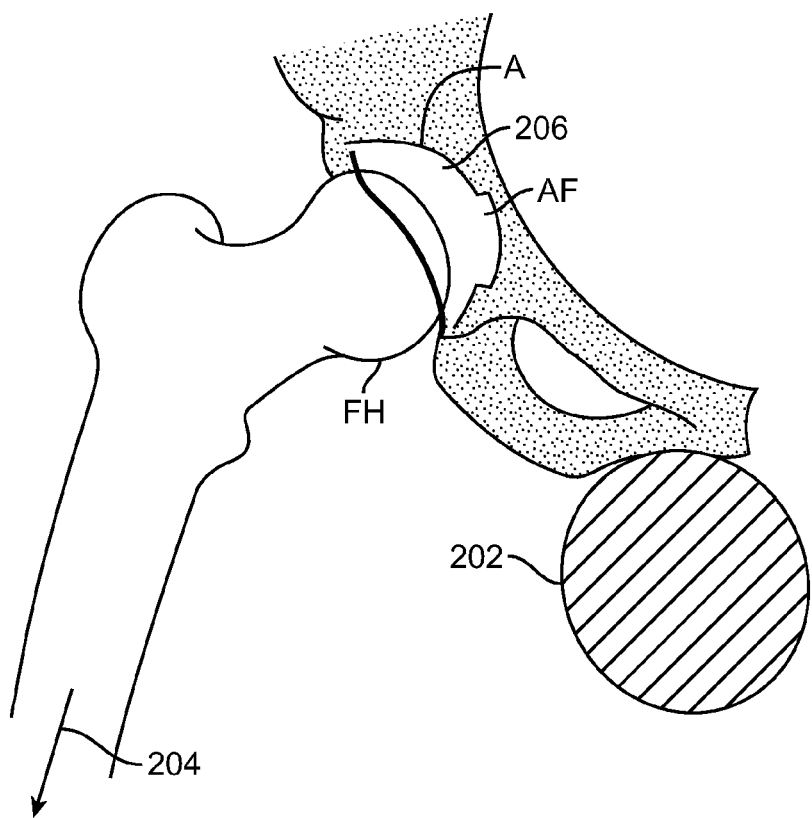
FIG. 2 illustrates distraction of a hip joint under traction.

FIG. 2 illustrates how traction 204 is conventionally applied to the patient's leg and against a post 202 positioned against the perineum region to distract the femoral head FH away from the acetabulum A thereby creating a space 206 between the two joint surfaces. This space 206 allows a surgeon to access the joint and perform diagnostic or therapeutic procedures. However, conventional distraction tables are often rigid systems affixed to an operating room table and they are not easily adjustable. Thus, once distraction is obtained, conventional distraction tables are locked into position to maintain the distraction and have very limited capability for further manipulation of the joint to provide greater access to the joint or access to different regions of the joint space. For example, in the case of a hip joint, it would be desirable to be able to flex, extend, abduct, adduct, laterally rotate or medially rotate the joint through a broad range of motion so that access and visibility to the joint space and adjacent structures may be adjusted while the joint is distracted. In addition, even with distraction tables that allow some manipulation of the hip joint, because traction must be maintained, it is not possible using conventional distraction tables to bend the patient's knee. When the leg is straight, the hip joint may be flexed up to approximately 20°, but bending the knee allows the hip joint to be flexed even more, thereby allowing even greater access to the joint. Additionally, the pressure exerted by the post 202 against the perineum can result in post operative complications and therefore it would be desirable to provide improved methods and devices for distraction of joints.

Figure 3:
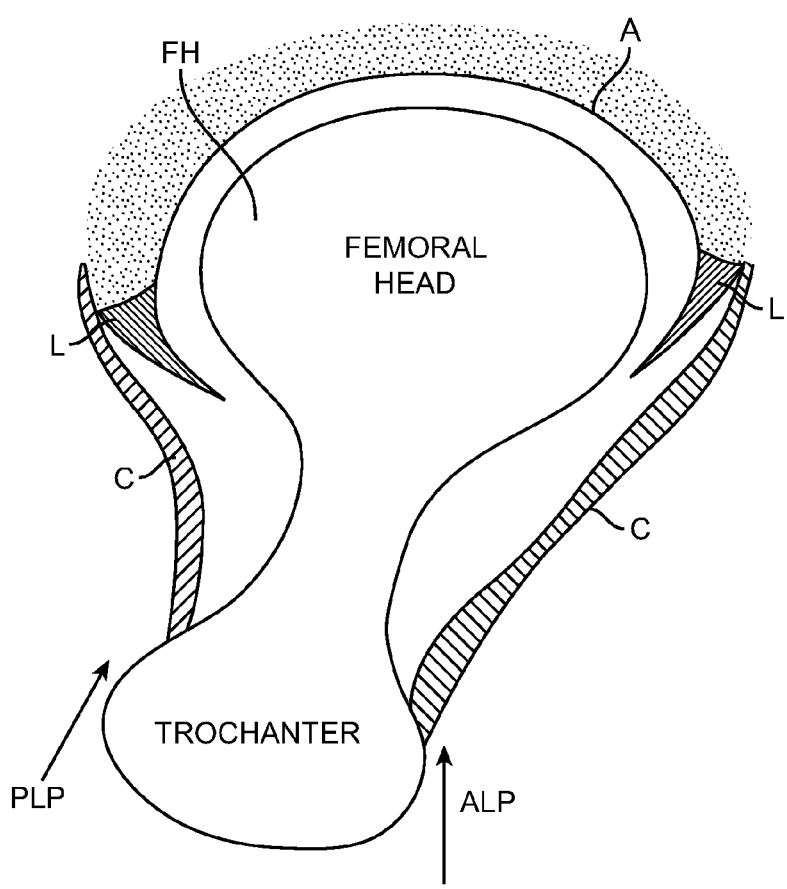
FIG. 3 illustrates a top view of a hip joint.

In order to overcome the challenges of current distraction techniques, the present invention provides methods and apparatus for internal distraction of a joint that do not require external traction to be applied. In preferred embodiments the invention provides a hydraulic distraction device, e.g. a balloon, that may be placed into the interior of the joint between the opposing bones and inflated with a fluid to distract the joint. FIG. 3 illustrates some of the possible entry portals for delivering a balloon to the hip joint. FIG. 3 is a top view of a hip joint in which the femoral head FH rests against the acetabulum A. The joint space is covered by the capsule C and the labrum L. Access to the hip may be obtained by introducing a balloon in a posterolateral portal PLP along a side and posterior to the joint or an anterolateral portal ALP along a side and anterior to the joint. The balloon and related instruments may be delivered into the joint space through a port or cannula, or using minimally invasive techniques such as Seldinger-like or percutaneous introduction, or a cutdown procedure may be used. FIGS. 4A-4E illustrate how access to the hip joint may be obtained.

Figure 4A:
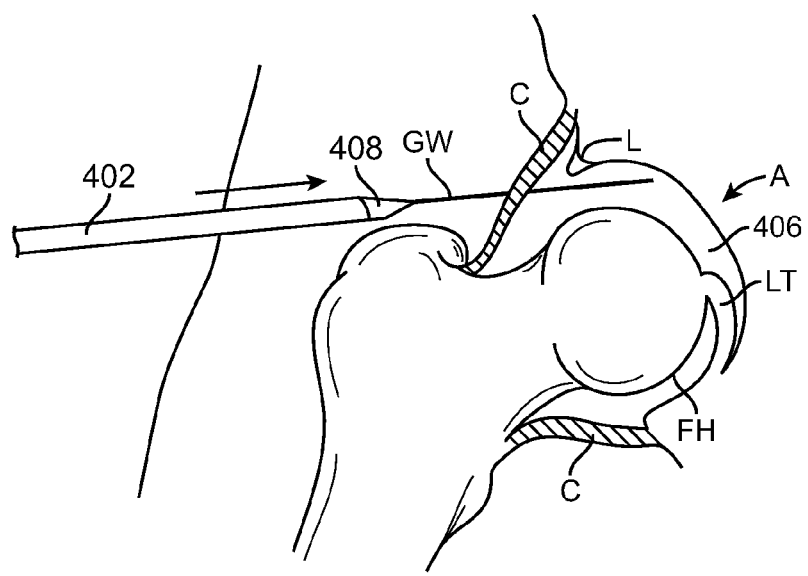
FIGS. 4A-4G illustrate balloon distraction of a hip joint.
Figure 4B:
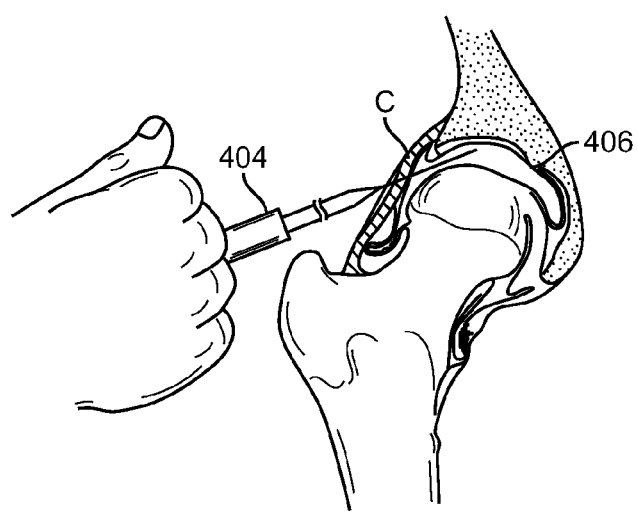
Figure 4C:
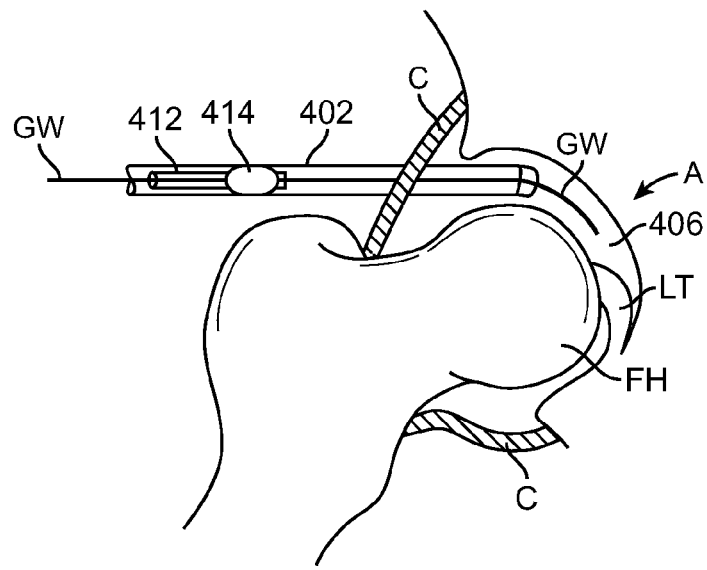
Figure 4D:
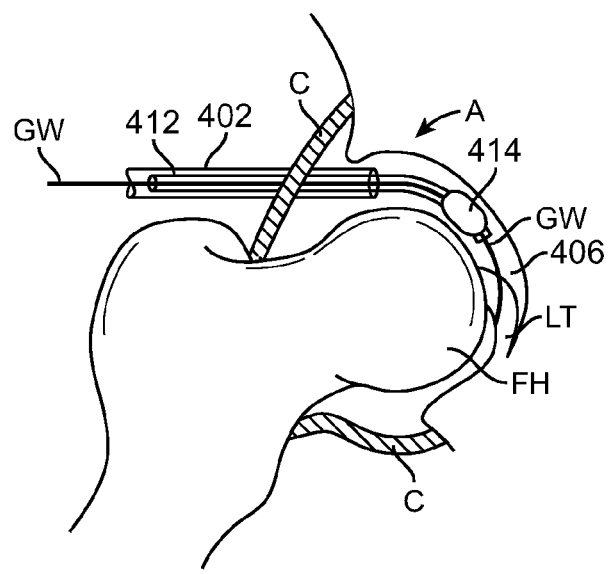
Figure 4E:
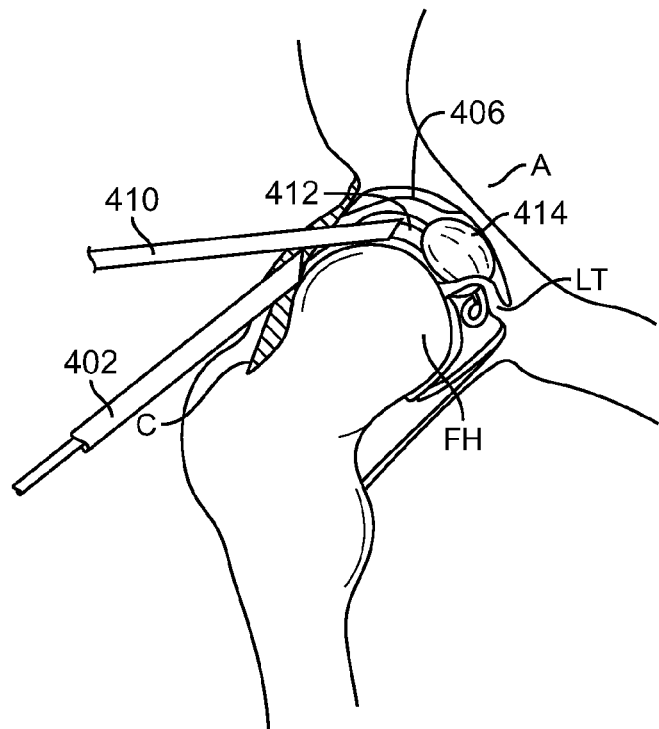

Percutaneous access to the hip joint begins with a needle such as a 17 gauge needle (not illustrated) advanced through the skin and past the capsule C into the joint space 406. This may be observed under fluoroscopy or other imaging systems. The capsule is then optionally distended by injecting saline into the space. Once the needle is in place, a guidewire GW or switching wire is advanced through the needle into the joint space. The needle is then withdrawn, leaving the guidewire GW in place. The guidewire GW serves as a rail over which other instruments may be delivered to the joint space. In FIG. 4A, a tubular sheath or cannula 402 having a tapered end 408 is advanced over the guidewire GW into the joint space 406. The tapered end 408 helps the sheath to pass through and penetrate layers of the capsule C. A balloon catheter (FIG. 4C) is nested inside sheath 402 and the sheath constrains the balloon in order to help keep balloon profile to a minimum as well as to provide protection to the balloon during delivery. Optionally, in FIG. 4B a syringe with needle 404 or other injection device may be used before, during or after delivery of the balloon catheter to inject fluid such as saline into the joint space in order to help distend the capsule C, thereby creating additional working space and facilitating passage of the guidewire and/or catheter through the capsule. Breaking the seal created by the labrum and introducing fluid pressure into the central compartment also helps to distract the joint sufficiently to allow insertion of balloon catheter 412. The sheath 402 carries a catheter 412 with deflated balloon 414 into the joint space as seen in FIG. 4C. Once the sheath 402 is positioned, the catheter 412 having deflated balloon 414 on its distal end may be advanced through the sheath and exposed (or alternatively, the sheath may be retracted) as seen in FIG. 4D. The distal end of the catheter may have an atraumatic distal tip 416 that is adapted to facilitate advancement of the catheter around the curved joint space without causing damage to the articular cartilage or surrounding tissues. Additionally, the balloon 414 is advanced and positioned posterior to the ligamentum teres LT without causing damage to the ligament or associated tissues. In other situations, it may be desirable to position the balloon anterior to the ligamentum teres and in still other situations a forked balloon may be used to pass on both sides of the ligamentum teres (as disclosed below). The balloon 414 is then expanded with saline, contrast media, a combination of the two, or another fluid may be used including gaseous inflation fluids. This may be seen in FIG. 4E. Once expanded, the balloon distracts the femoral head FH away from the acetabulum A, increasing the joint space 406. Balloon expansion is performed without causing damage to the ligamentum teres, nearby vasculature, nerves, or other adjacent tissues. Preferably, the balloon will create a gap of about 10 to 12 mm or more. An arthroscopic instrument 410 may then be advanced into the joint space through the same cannula or a different cannula, so that diagnostic or therapeutic procedures may be performed on the joint or surrounding tissues.

Figure 4F:
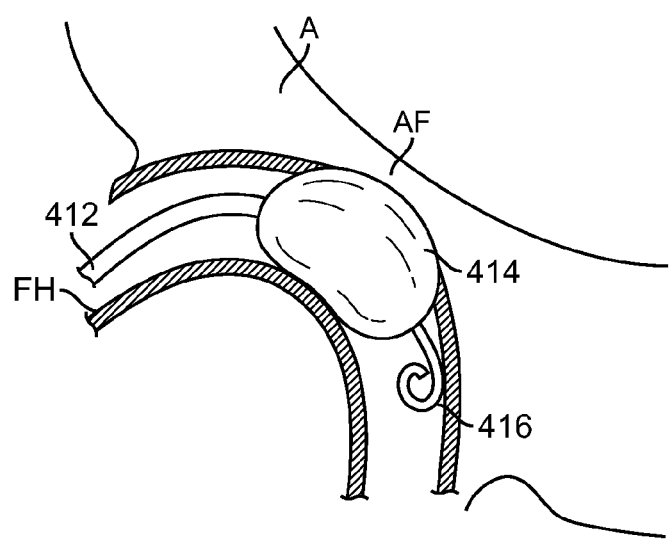
Figure 4G:
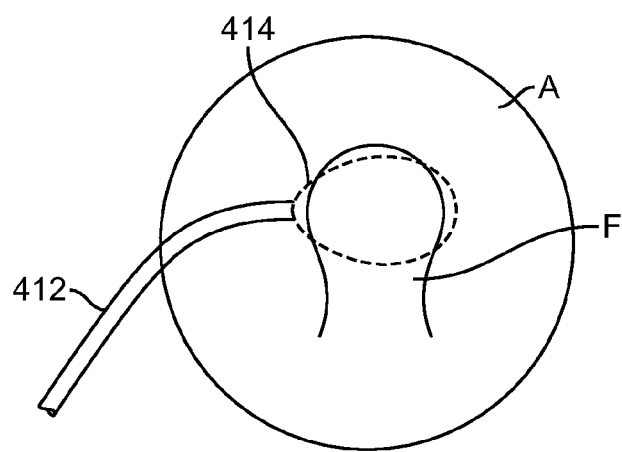

In preferred embodiments, the balloon is advanced into the joint and expanded so that when expanded, it seats in the acetabular fossa AF. The acetabular fossa is a concave region in the acetabulum and provides a natural concavity into which the balloon may be seated to stabilize the balloon and inhibit its movement as it expands and as the joint is manipulated. FIG. 4F more closely illustrates seating of an expanded balloon in the acetabular fossa. The balloon remains seated in the fossa during inflation and distraction of the joint. FIG. 4G is a view of the acetabulum A and the fossa F looking into the joint space with the femoral head removed. The balloon 414 indicated by dotted lines is seated in the fossa with minimal overlap onto the surrounding surface of the acetabulum. Additionally, while the balloon is inflated and the joint is distracted, the hip may be manipulated in order to alter joint position and increase access to the joint space as will be discussed in greater detail below.

Figure 5A:
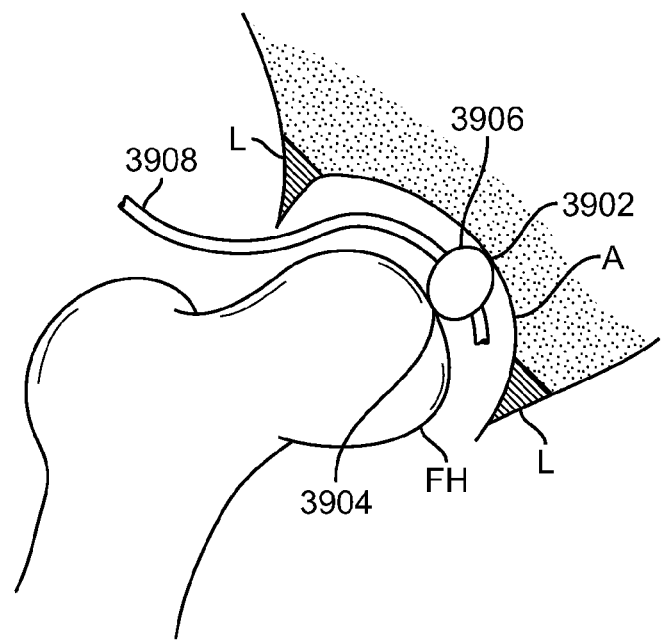
FIGS. 5A-5C illustrate various balloon contact areas.
Figure 5B:
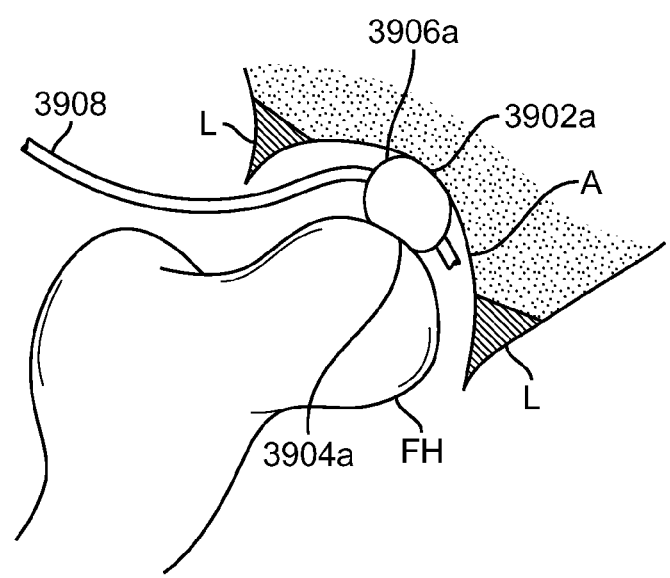
Figure 5C:
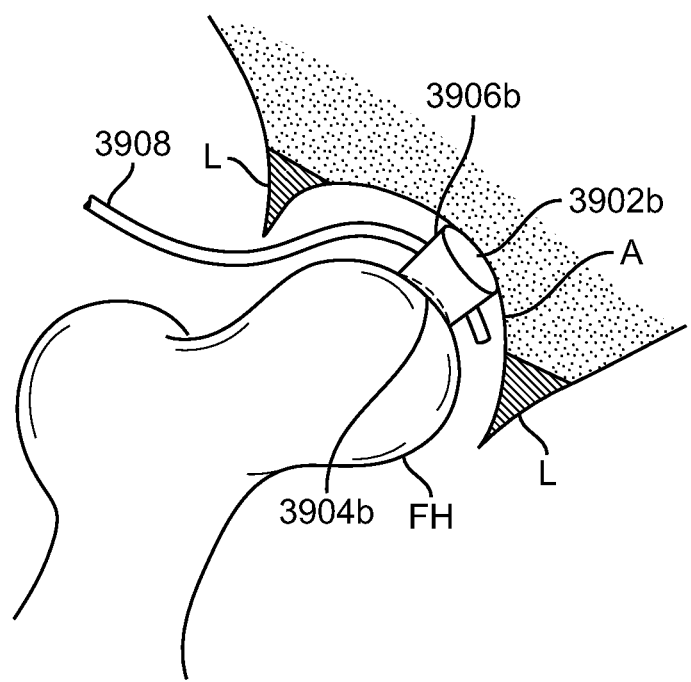

Preferably, the area of the balloon that contacts the joint surfaces will be minimized in order to allow maximum visibility of, and access to the joint tissues. At the same time, because the distraction force provided by the balloon is the product of the balloon contact area and the balloon pressure, sufficient contact area must be provided in order to avoid excessively large balloon pressures. FIG. 5A illustrates the situation where contact area is minimized. In FIG. 5A, a spherically shaped balloon 3906 near the distal end of a shaft 3908 is inflated in the joint space between the acetabulum A and the femoral head FH. The spherically shaped balloon 3906 is inflated and contacts the joint surfaces at a point of contact 3902 on the acetabulum A and also a point of contact 3904 on the femoral head FH. This provides relatively unobstructed access to the joint space. However, because the contact area 3902, 3904 is very small, the balloon pressure will be very high in order to provide adequate force to distract the joint. Preferably, the balloon will be constructed of a generally inelastic, non-distensible material such that the balloon may be inflated to a fixed volume. FIG. 5B illustrates what happens when such a balloon is inflated. The contact areas 3902a, 3904a of the balloon 3906a flatten out and conform to the joint surfaces as the balloon expands. Because the balloon flattens out, access to the joint space is more limited than in FIG. 5A, yet because the contact area 3902a, 3904a is greater, lower balloon pressures are required to distract the joint. FIG. 5C illustrates an embodiment that balances the balloon contact area with joint access. In FIG. 5C a cylindrically shaped balloon 3906b is coupled to a shaft 3908 and advanced to the joint space between the acetabulum A and the femoral head FH. The cylindrical body of the balloon 3906b provides a relatively large flat upper contact area 3902b and a relatively large flat lower contact area 3904b that engage the acetabulum A and femoral head FH, respectively. The contact areas 3902b, 3904b are sufficiently large so that reasonable balloon pressures may be employed during distraction while at the same time, still allowing relatively unobstructed access to the joint space. Preferably the total area of contact of the balloon against each joint surface will be no more than about 50% of the total area of that joint surface. In the case of the hip joint, the contact area is preferably no more than about 50%, and more preferably less than about 30% of the total surface area of the acetabulum outside the fossa, when the balloon is inflated.

In a preferred embodiment, the balloon contacts the acetabulum over a total contact area no more than about 800 mm$^2$, and preferably the contact area is no more than about 50%, and more preferably less than about 30% of the surface area of the acetabulum outside the fossa when the balloon is inflated. On the other hand, the balloon contact area will not be so small that extremely high pressures are required to distract the joint, thereby requiring balloons with extremely high burst pressures. In preferred embodiments the balloon is capable of generating sufficient force to distract the joint, preferably generating at least 30 pounds of force and more preferably at least 50 pounds of force, and most preferably at least 75 pounds of force with pressure not exceeding about 20 atmospheres (300 psi), more preferably not exceeding about 7 atmospheres (100 psi), and most preferably not exceeding about 5 atmospheres (75 psi). Thus, in preferred embodiments, the total contact area of the balloon on each of the opposing joint surfaces will be about 0.3 to 1.2 square inches (200 to 800 mm$^2$). Additional balloon embodiments are disclosed below. Because of these desired operating conditions, most commercially available balloon catheters would not be suited for distracting a joint. In particular, cardiovascular balloons would generally not be able to distract the joint as far as desired at sufficiently low pressures. Moreover, often, many of the commercially available balloons are very long and therefore would not fit properly in the joint space, would not seat securely in the fossa, or they would obstruct the work field or they could be ejected from the joint during inflation.

Figure 6:
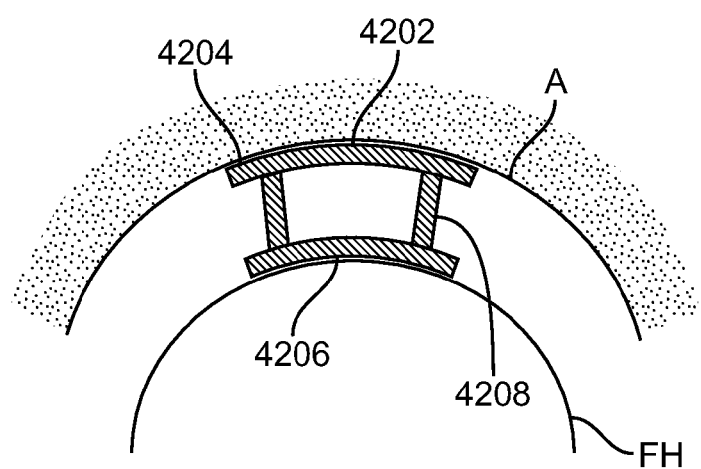
FIG. 6 illustrates a support for maintaining joint distraction.

After the joint has been distracted, a spacer 4202 as illustrated in FIG. 6 may be placed in the joint space in order to maintain separation of the joint surfaces after the balloon distraction device has been removed. The spacer 4202 includes an upper surface 4204 that has a curvature matching that of the acetabulum A and a lower surface 4206 that has a curvature matching that of the femoral head FH. Having a matching contour helps prevent damage to the joint surfaces and more evenly distributes the forces along the contact surfaces. The upper and lower surfaces may be padded or covered by a soft material to minimize trauma. Both surfaces are separated by posts 4208. Posts 4208 may have round, elliptical, square or other cross sectional profiles. Posts 4208 may be vertically movable or adjustable to change the distance between the upper and lower surfaces. The spacer 4202 may be surgically implanted or more preferably, delivered arthroscopically through a cannula and then assembled or expanded in situ. The spacer may have a locking mechanism to ensure stability of the assembly after it has been positioned. In some cases, it may be advantageous to overinflate the distraction balloon to distract the joint even further, thus providing additional space for delivery and placement of the spacer 4202. The distraction device can then be deflated once the spacer is in place. Removal of the spacer 4202 can be accomplished by reintroducing and expanding the distraction device enough to allow the spacer 4202 to be removed from the joint space. Alternatively external distraction may be used to insert or remove the spacer.

Figure 7:
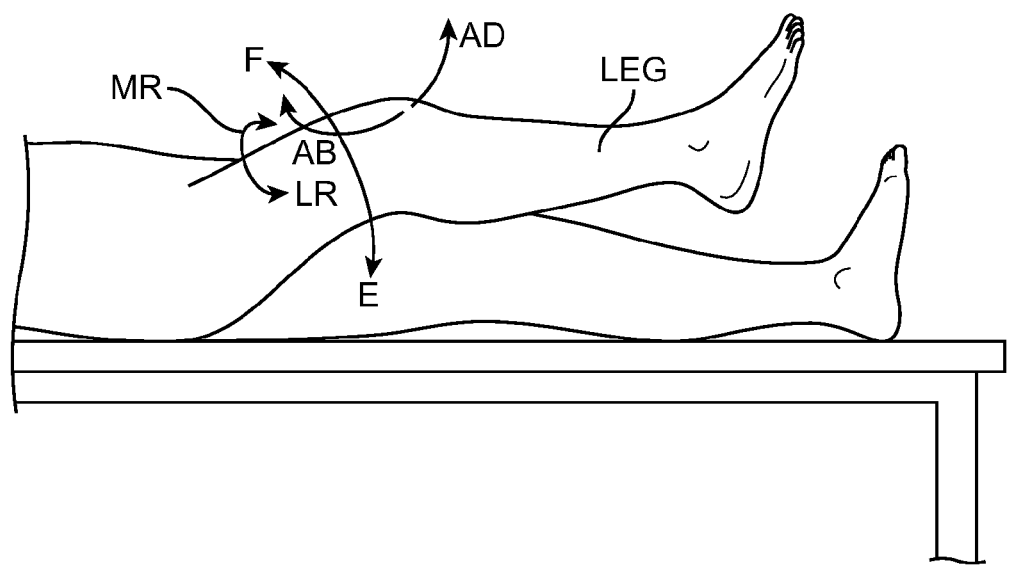
FIG. 7 illustrates various axes of movement about the hip joint.
Figure 8:
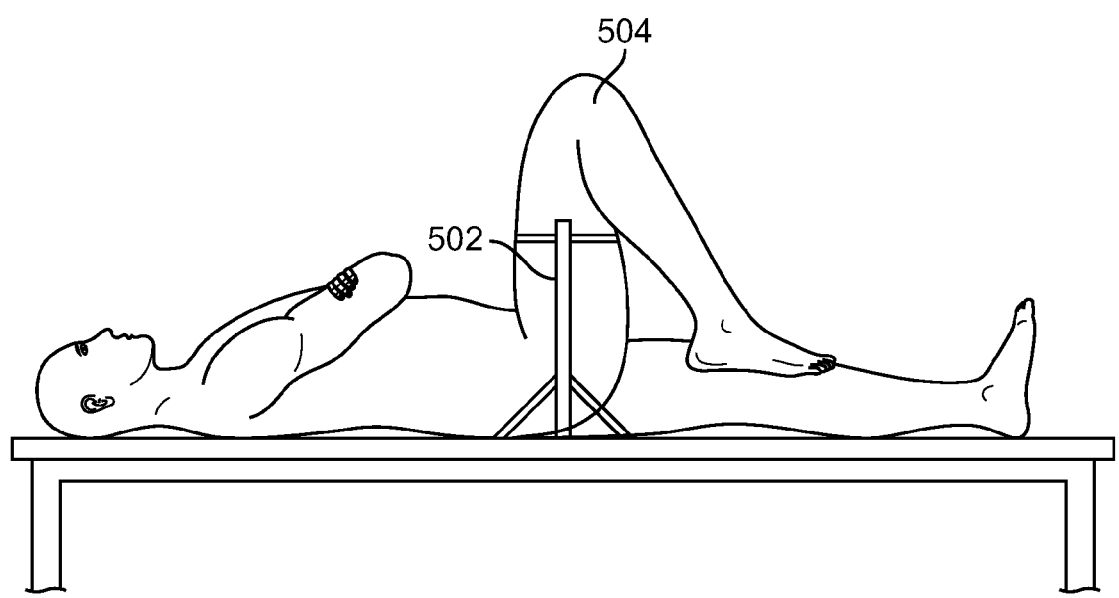
FIG. 8 illustrates use of a leg brace to hold a patient's distracted hip in a desired position.

Referring back to FIGS. 4E-4F, with balloon 414 in place and the joint distracted, the joint may be manipulated to obtain optimal visibility and access to the target structure in the joint. Such manipulation may include flexion (bending of the femur anteriorly and superiorly) and extension (straightening) of the hip joint, lateral (external rotation away from the center of the body) and medial (internal rotation toward the center of the body) rotation, as well as abduction (lateral movement away from the body midline) and adduction (medial movement toward the body midline) of the joint. The size, shape and curvature of the expanded balloon will permit manipulation of the hip joint in the distracted configuration without significant movement or dislodgement of the balloon. In an exemplary embodiment the balloon will be a non-bifurcated compact shape with a uniformly convex, preferably spherical, outer surface, positionable in the center of the joint (e.g. fossa) such that contact with the joint surfaces in concentrated within a central region of the joint, allowing the surfaces around the balloon near the periphery of the joint to be unconstrained. This shape provides a fulcrum about which the opposing bones can rotate and minimizes any impedance of joint movement. Additionally, the knee 504 may be flexed or extended to allow greater range of motion in the hip joint. Typically, the hip may be rotated laterally up to at least about 30°, rotated medially up to at least about 40°, extended up to at least about 20°, flexed up to at least about 140°, abducted up to at least about 50° and adducted up to at least about 30°. With the knee bent and the hip flexed, lateral rotation may be increased up to about 50°, abduction increased to about 80° and adduction decreased to about 20°. FIG. 7 illustrates flexion F, extension E, medial rotation MR, lateral rotation LR, abduction AB and adduction AD of a patient's hip joint. In addition to providing enhanced access to the joint space, manipulation of the hip joint also relaxes various tissues to allow better access to the joint. For example, flexion of the hip joint releases tension on the anterior joint capsule to allow better access to the labrum and other adjacent joint structures. Thus, the balloon distraction procedure is advantageous over traditional traction methods of distracting a joint since under external traction, conventional methods prevent substantial flexion of the hip joint to relax the capsule. Moreover, the present method is also advantageous over conventional distraction methods since it allows for additional manipulation of the hip joint while the joint is distracted. Once the hip joint has been distracted and manipulated over a broad range of motion into a desired position to provide the desired access to the joint space, a leg brace 502 as illustrated in FIG. 8 may be used to hold the patient's leg in a desired position. One end of the leg brace may be attached to the patient's thigh or lower leg, and the other end attached to a surgical table or other support structure. The leg brace may also be free standing or fixed to the patient's upper body and/or lower leg.

Figure 9A:
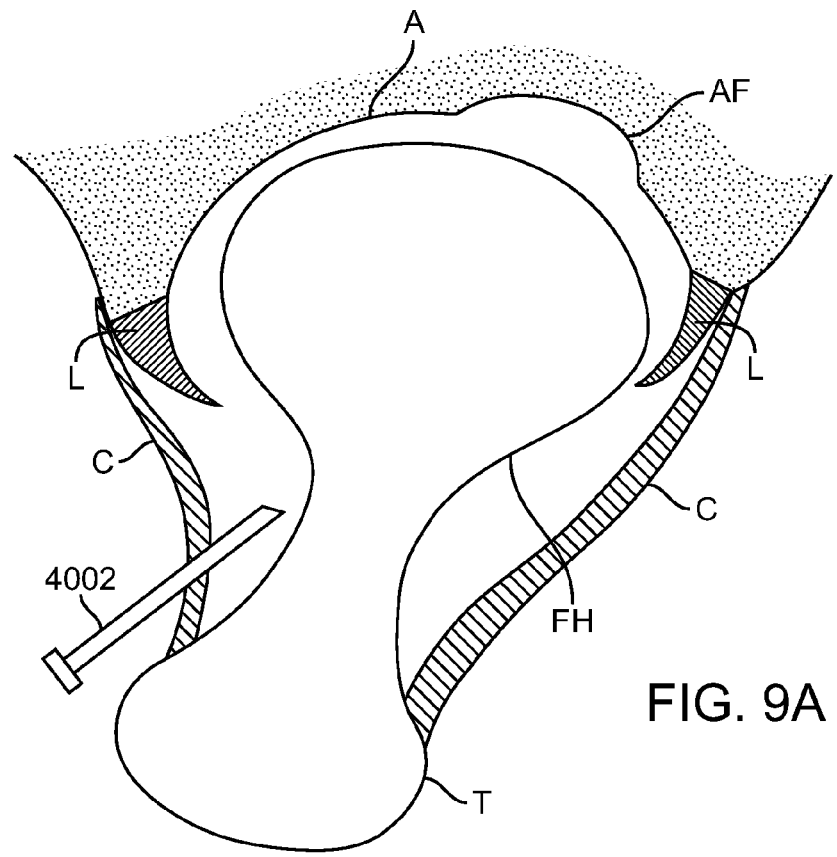
FIGS. 9A-9I illustrate another embodiment of balloon distraction of the hip joint.
Figure 9B:
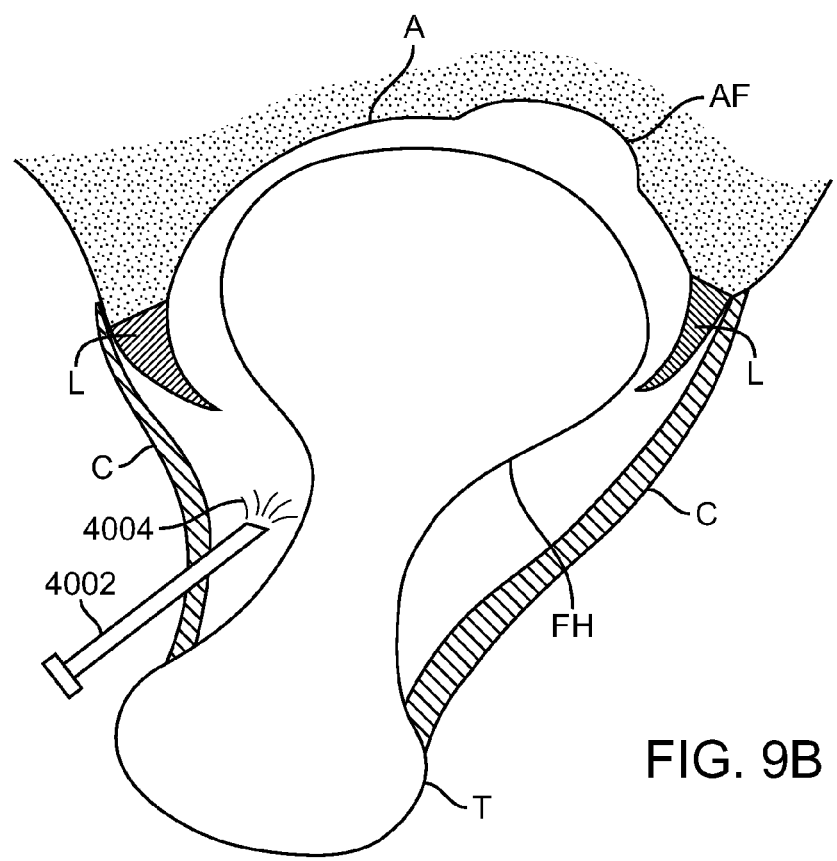
Figure 9C:
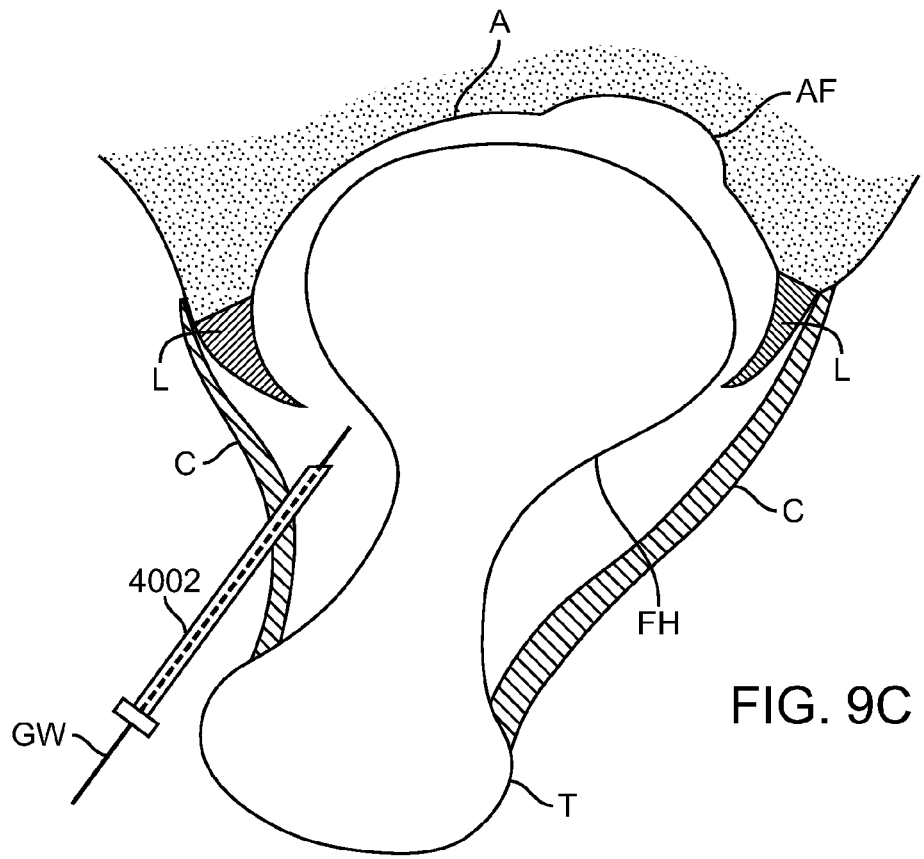
Figure 9D:
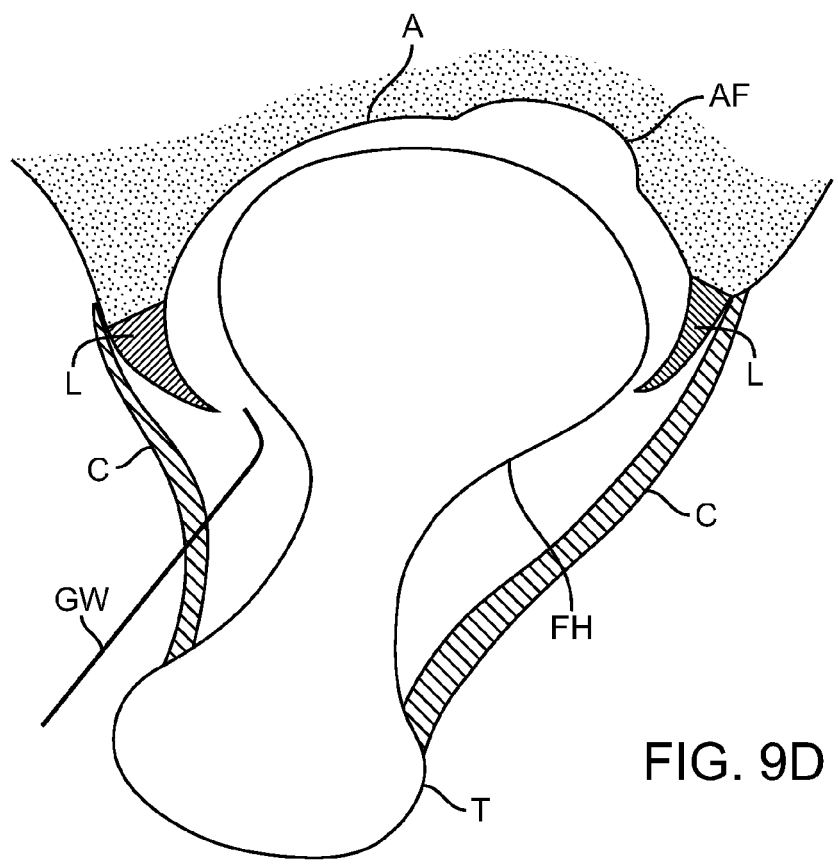
Figure 9E:
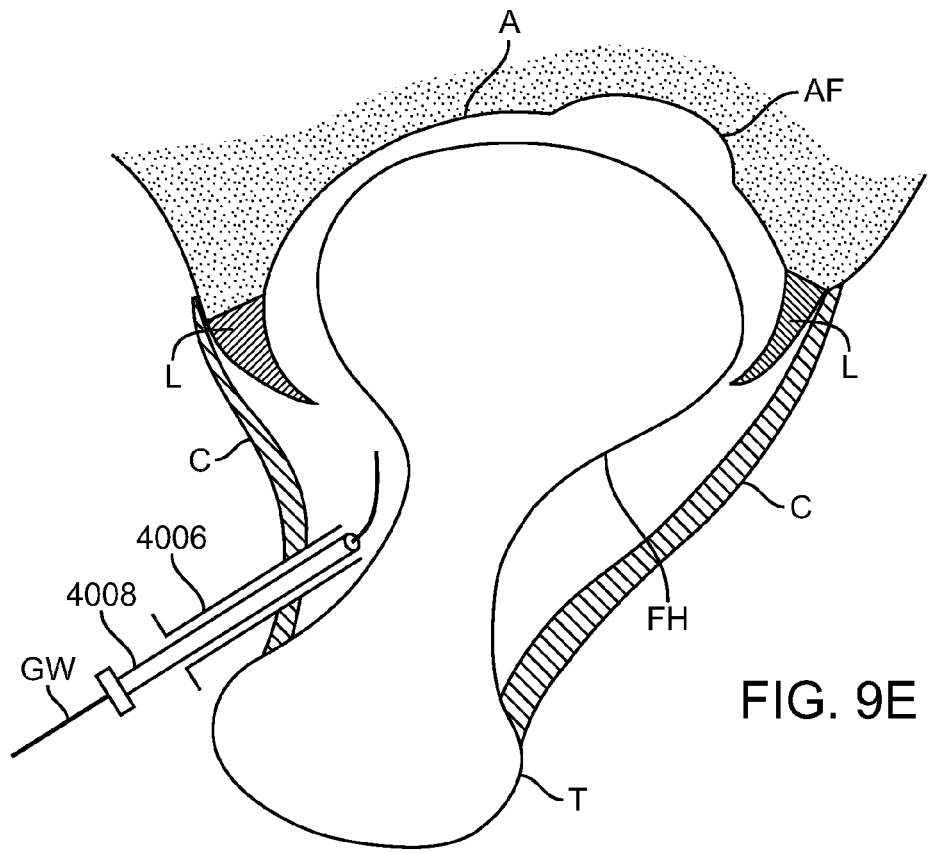
Figure 9F:
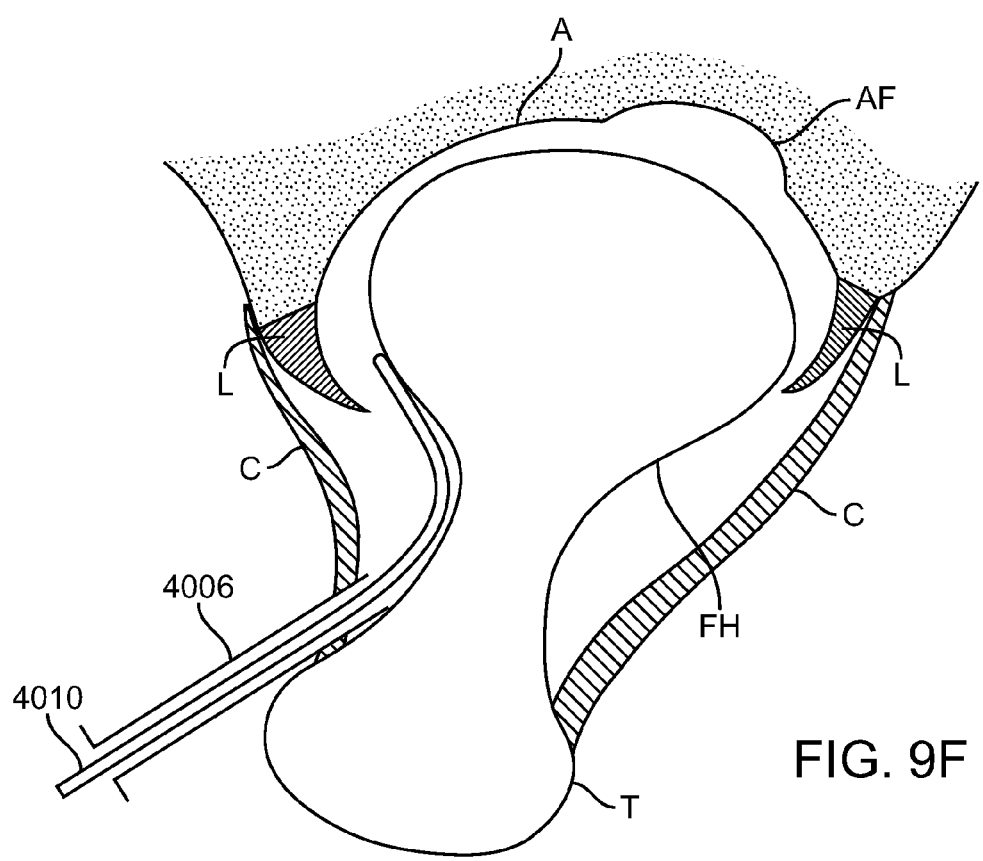

FIGS. 9A-9I illustrate a preferred embodiment of a method for accessing and distracting a hip joint. FIG. 9A is a top view of the hip joint formed by the femur bone having a trochanter T and femoral head FH disposed in the acetabulum A. The acetabulum has a depressed region known as the acetabular fossa AF where the ligamentum teres (not illustrated for clarity) is attached. The joint also consists of the labrum L and is surrounded by a capsule C. In FIG. 9A, a needle 4002, preferably 17 G, having a sharp removable inner core, is placed under fluoroscopic guidance through the capsule into the peripheral compartment of the joint. An anterolateral or posterolateral port may be used for joint access. The needle is preferably introduced parallel to and touching the femoral neck and generally tangent to the major curve of the femoral head. This helps ensure that the needle is inserted into the peripheral compartment safely and helps line the needle with the point where the labrum and femoral head touch. Once in place, the sharp inner core is removed and FIG. 9B illustrates injection of saline 4004 through the needle 4002 into the peripheral compartment in order to distend the capsule and create more working space. A guidewire GW or switching wire is then advanced through the needle 4002 into the joint space as seen in FIG. 9C and then the needle is removed, leaving only the guidewire GW in place, as illustrated in FIG. 9D. Next, FIG. 9E shows a cannulated obturator 4008 advanced over the guidewire GW into the joint space. The cannula 4006 is preferably 5 mm in diameter and is a split cannula. After the balloon is introduced, the split cannula can be removed and reintroduced alongside the balloon and the same access port can be used to insert a scope or other arthroscopic tool. The obturator 4008 is removed from the cannula 4006, and then an introducer 4010 is placed into the cannula 4006. The introducer is preferably fabricated from a polymer so that it does not damage the joint surfaces or other tissue, and is flexible and pushable so that it may be advanced past the labrum L into the central compartment of the joint space, as illustrated in FIG. 9F. The introducer 4010 may be about 2-4 mm wide and have a thickness of about 1-3 mm and is sized to receive a balloon distraction device. The introducer may also have a central lumen to allow fluid to be dispersed from the tip. In some embodiments, the introducer may be pre-shaped to the contour of the femoral neck to ease insertion.

Figure 9G:
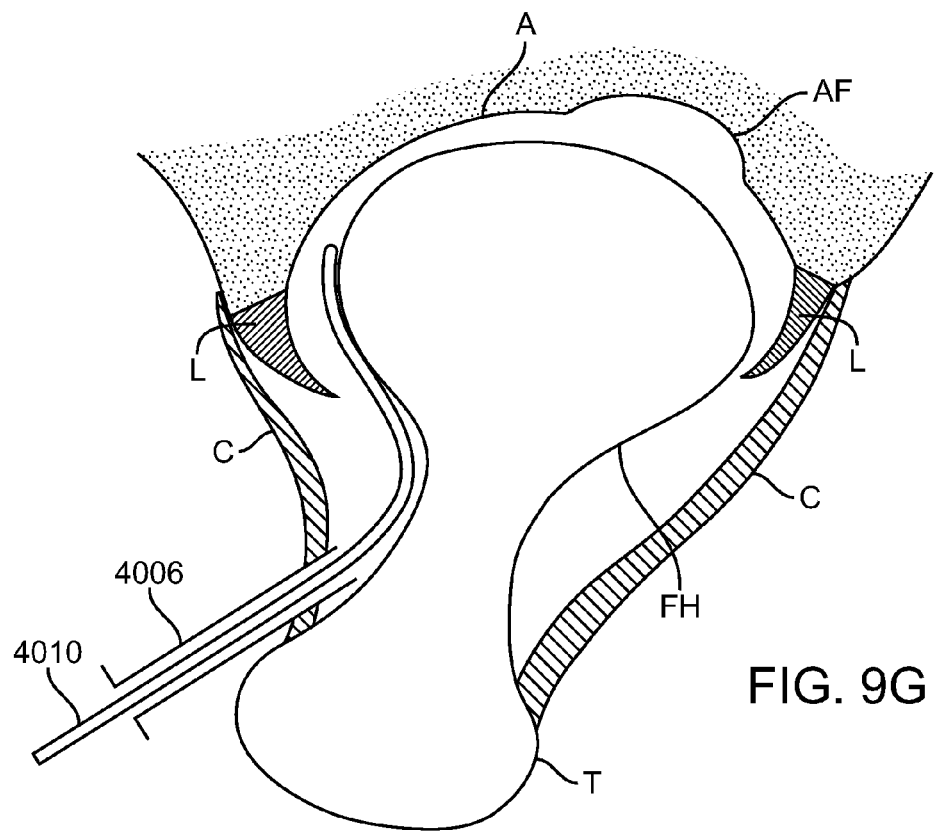
Figure 9H:
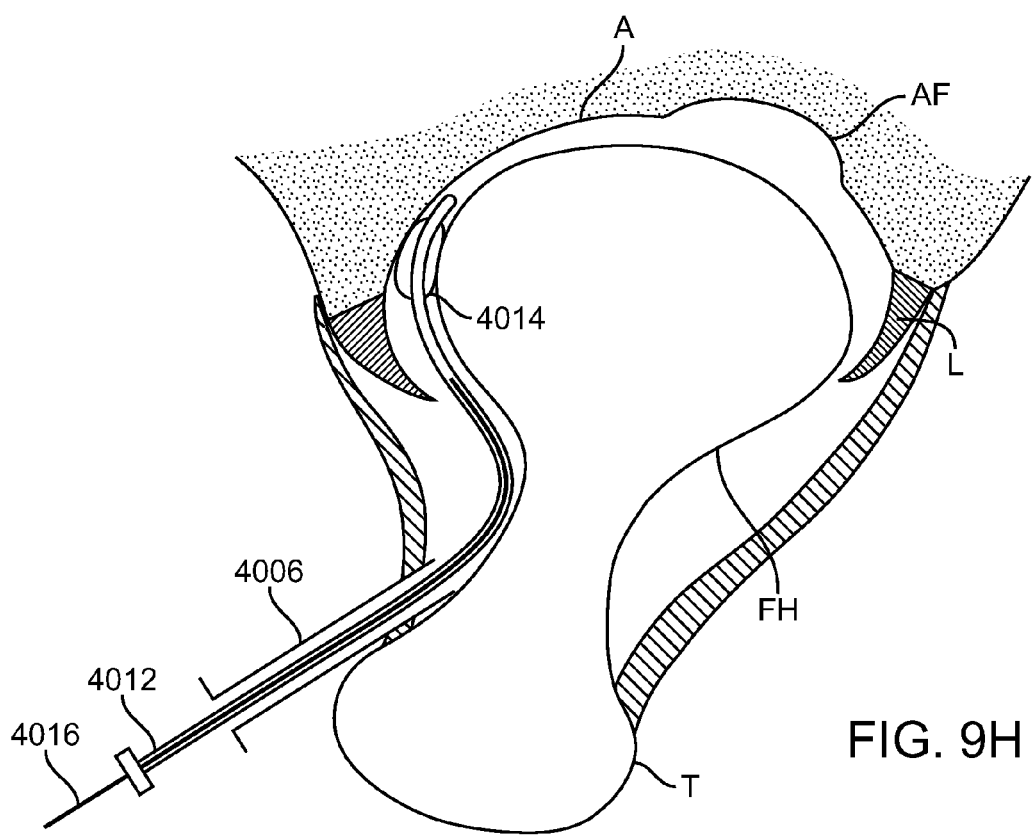
Figure 9I:
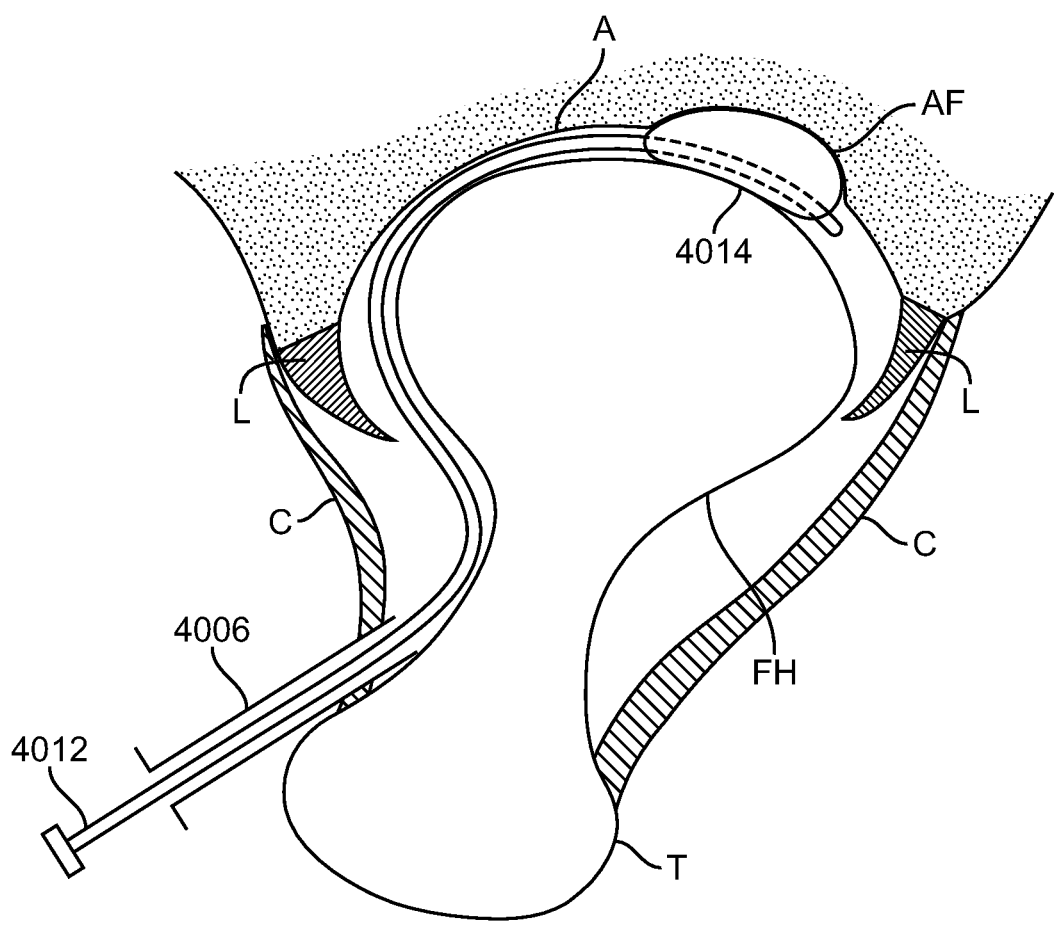

The introducer 4010 is then advanced along the contour of the femoral neck under the labrum L until the vacuum seal between the labrum L and femoral head FH is broken. The tip of the introducer 4010 may be flat in order to help it pass under the labrum. Slight manual traction or manipulation to the hip joint may be applied in order to help the introducer pass under the labrum. Fluid from the introducer may also be injected to help crossing the labrum. The saline 4004 injected into the joint space may also include a surfactant to help ease entry of the fluid into the central compartment in order to break the vacuum seal. Once the seal of the labrum L and femoral head FH is broken, the introducer 4010 is advanced until its tip is within the central compartment of the joint as seen in FIG. 9G. Advancement of the introducer may be visualized under fluoroscopy to help with guidance. The distraction device 4012 having an expandable balloon 4014 near its distal end is then advanced through the introducer 4010 into the central compartment and the introducer 4010 is removed. The balloon distraction device 4012 optionally may also have a stiffening shaft 4016 or metal stylet the help provide stiffness to the device during advancement. The stiffening shaft 4016 is advanced within a lumen in the distraction device 4012 until the distal end of the stiffening shaft 4016 is positioned at the edge of the central compartment while the deflated balloon 4014 is advanced into the central compartment, as illustrated in FIG. 9H. The balloon 4014 is advanced to a desired location in the joint space, preferably the fossa AF. The metal shaft 4016 is then removed and the balloon 4014 is inflated to distract the joint as illustrated in FIG. 9I. Preferably the joint is distracted about 10-12 mm, which may in fact actually require the balloon to be expanded to a greater diameter, e.g. 17 mm or more, due to the concavity of the fossa and the directional nature of the distraction forces.

Figure 10A:
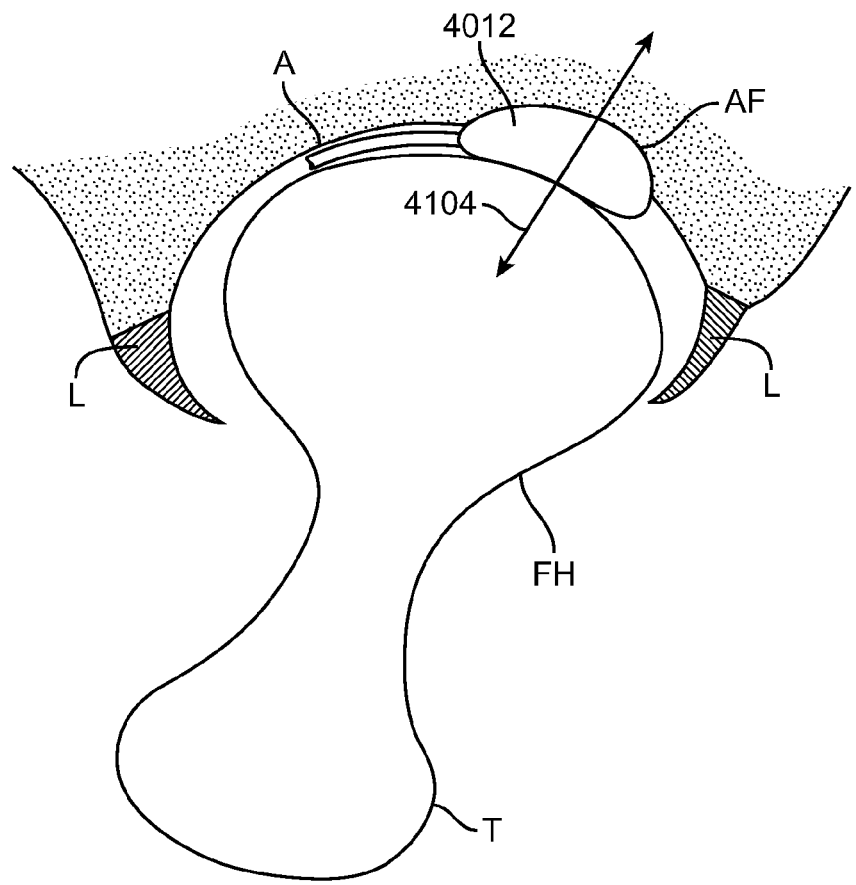
FIGS. 10A-10B illustrate balloon distraction vectors.
Figure 10B:
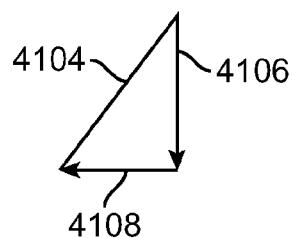

For example, FIG. 10A illustrates expanded balloon 4102 distracting a hip joint along vector 4104 which is generally orthogonal to the acetabulum and also orthogonal to the femoral head. When vector 4104 is broken down into its horizontal 4108 and vertical 4106 components as shown in FIG. 10B, it is clear that the actual horizontal or vertical displacement will be much less than total displacement along vector 4104. Thus, in order to obtain a desired vertical or horizontal displacement of the joint, the joint must be distracted an even greater amount orthogonal to the joint surfaces. Simple trigonometry may be used to calculate the components of the distraction vector 4104. In addition, the distraction balloon may be deflated and moved within the joint space and reinflated in order to provide a different distraction force vector which would result in a different amount or direction of the distraction.

The distraction balloon may have various shapes and/or features to make it susceptible to seating and being retained in the fossa. For example, in FIG. 11A, balloon 606 has a overall total axial length which includes the working length 602 plus the length of the proximal and distal tapered regions. The working length 602 is the portion of the balloon which contacts the joint surface and does not include the tapers. The balloon has expanded diameter 604, preferably about 15-30 mm, more preferably about 20-27 mm. The working length 602 is preferably in the range of about 0.8 to 1.3 and more preferably in the range of about 0.75 to 1.25 times as large as the diameter 604, and in a particularly preferred embodiment the length is substantially equal to the diameter. This results in a short, generally cylindrical, fat balloon 606 which allows seating in the fossa and because of its compact size, also permits visualization and access around the entire balloon to the surfaces of the joint behind the balloon. This shape also helps to ensure that the entire balloon can be advanced distally from the introducer sheath or access cannula (if used) within the limited joint space.

Figure 11A:
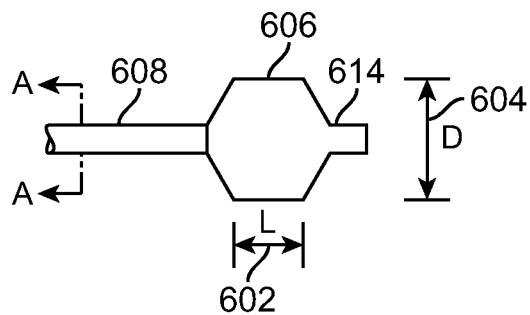
FIGS. 11A-11E illustrate various embodiments of distraction balloons and contact areas.
Figure 11B:
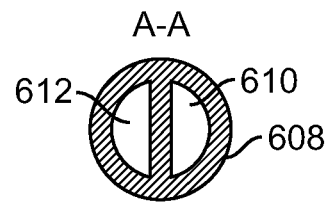
Figure 11C:
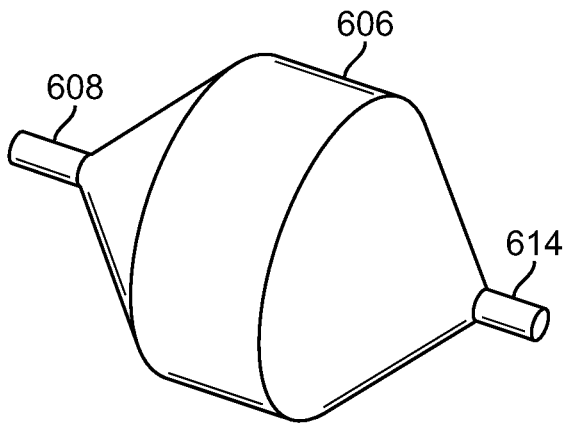
Figure 11D:
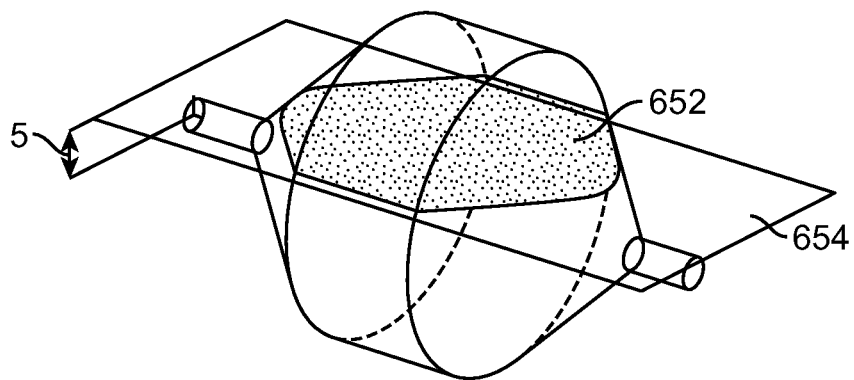

Balloon 606 is mounted to a catheter shaft 608 having a short distal tip 614. The balloon may be made of various materials, preferably inelastic, so that the balloon is non-compliant or semi-compliant and inflated to a generally fixed volume. Possible materials include Nylon, PET, polyurethane, or more compliant materials such as silicone or latex. Balloon wall thickness will preferably range from 0.0013" to 0.0020". The distal tip 614 may be a soft durometer polymer to prevent damage to the joint tissue. Other possible tip configurations which may be used with this embodiment or with any of the balloon embodiments disclosed herein are disclosed in further detail below. Shaft 608 may have a single inflation lumen or more preferably shaft 608 has at least two parallel lumens, one for balloon inflation 612 and a second lumen 610 for a guidewire, fluid infusion or passage of other instruments. The shaft may also have concentric lumens. A cross-section of shaft 608 taken along the line A-A in FIG. 11A is illustrated in FIG. 11B and FIG. 11C shows a perspective view of the balloon in FIG. 11A. FIG. 11D illustrates contact area 652 of this embodiment taken along a plane 654.

Figure 11E:
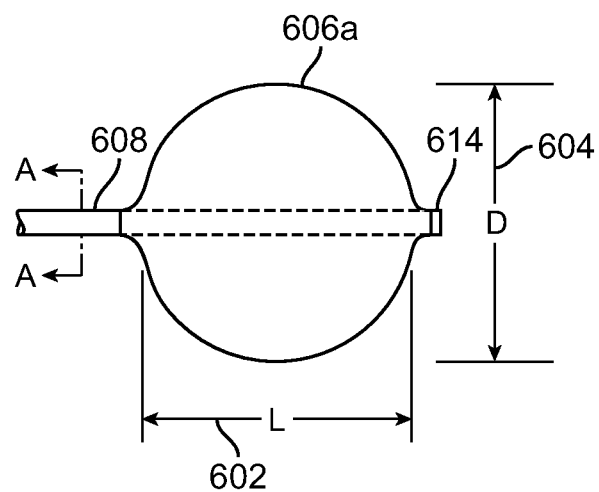

In a similar embodiment, instead of a cylindrically shaped body, the balloon is spherically shaped or near spherical. FIG. 11E illustrates a spherically shaped balloon 606a that has similar dimensions as the embodiment of FIG. 11A. Preferably the radius of curvature is substantially equal to or less than the radius of curvature of the joint surface. In the case of a hip joint, the acetabulum has a radius of curvature in the range from about 8 to 16 mm. Thus, the balloon engages the acetabulum in a single continuous region, preferably centered on the fossa.

Figure 12:
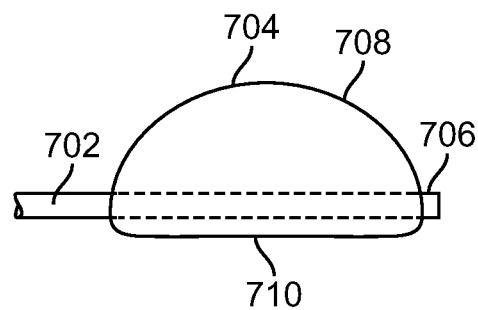
FIG. 12 illustrates another exemplary embodiment of a distraction balloon.

FIG. 12 illustrates another embodiment of a distraction balloon. In FIG. 12, balloon 704 has a semi-spherical, half-oval or mound shaped superior region 708 and an opposing substantially flat inferior region 710. The inferior region 710 may also have a significantly larger radius than the superior region, thereby resulting in a relatively flatter inferior region relative to the superior region. The balloon 704 may be structured so as to preferentially expand in an upward direction while the opposing inferior side remains relatively flat or of larger radius of curvature. The more bulbous, smaller-radius superior side is adapted to seat in the fossa while the inferior flatter side engages the femoral head. Balloon 704 is attached to shaft 702 which may have a single inflation lumen or may have any of the multilumen configurations described herein. The distal tip 706 is preferably a soft tip, but could also include any of the tip embodiments disclosed herein.

Figure 13A:
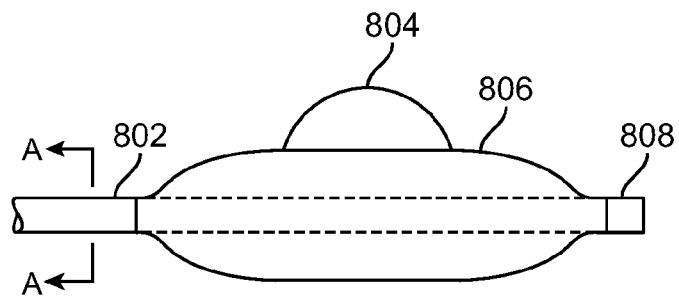
FIGS. 13A-13C illustrate another exemplary embodiment of a distraction balloon.
Figure 13B:
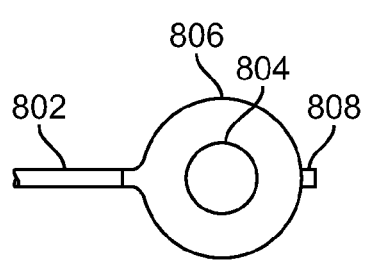
Figure 13C:
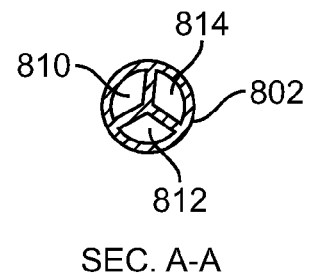

FIGS. 13A-13C illustrate still another embodiment of a distraction balloon. In FIG. 13A, the balloon includes a superior portion 804 and an inferior portion 806. The overall balloon is shaped like a fried egg or a flying saucer. The superior portion 804 has a central dome or central bulbous chamber and the inferior portion 806 is an annular, or donut shaped region surrounding or partially surrounding the central dome. Preferably, the superior portion 804 may be inflated independently of the inferior portion 806 and thus the two portions are fluidly isolated from one another by internal membranes in the balloon and thus at least two inflation lumens will be provided in the shaft 802. Alternatively, the two portions may be inflated together, in which case they are fluidly interconnected with one another and only a single inflation lumen is required in shaft 802. The superior and inferior regions may have a symmetrical shape both upward and downward, or either or both regions may have a flatter bottom side and a more rounded and distended upper side when inflated, with the upper side being adapted to conform to the concave surfaces of the fossa and acetabulum. The central chamber is sized and shaped to settle in the fossa while the annular portion is adapted to engage the joint surfaces surrounding the fossa, thereby stabilizing the balloon within the fossa. The catheter shaft may also have a soft atraumatic tip 808 or any of the tips disclosed herein. FIG. 13B illustrates a top view of the distraction balloon catheter of FIG. 13A and FIG. 13C illustrates a cross-section of shaft 802 taken along line A-A in FIG. 13A. In FIG. 13C, shaft 802 has three pie shaped lumens 810, 812, 814. Two of which may be used to inflate and deflate the superior 804 and inferior 806 portions of the balloon and the third lumen may be for a guidewire, irrigation or for other instruments.

Figure 14A:
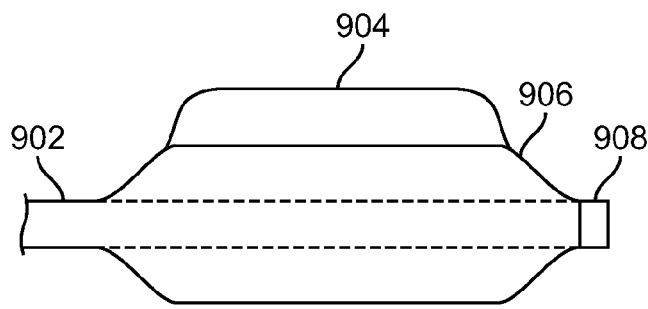
FIGS. 14A-14B show another exemplary embodiment of a distraction balloon.
Figure 14B:
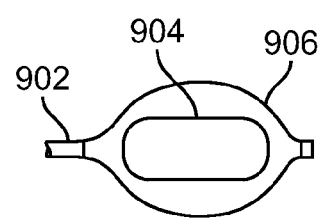

FIGS. 14A-14B illustrate yet another embodiment of a distraction balloon catheter. In FIG. 14A, the balloon includes a pancake or discoid shaped or lollipop shaped main body 906 with a longitudinal ridge or tubular chamber 904 extending axially along the superior side of the main body 906. In alternative embodiments, the inferior surface of the main body may also include a longitudinal ridge or tubular chamber extending axially therealong. The ridge protrudes from the surface of the main body to facilitate seating of the balloon in the fossa. As in other embodiments, the main body 906 may be inflated together with or independently of the tubular chamber 904. The balloon is attached to the distal portion of a shaft 902 and includes a soft atraumatic tip 908. The shaft may have any of the lumen configurations described herein and the tip may include any of the tip configurations described herein. FIG. 14B is a top view of the balloon depicted in FIG. 14A.

Figure 15:
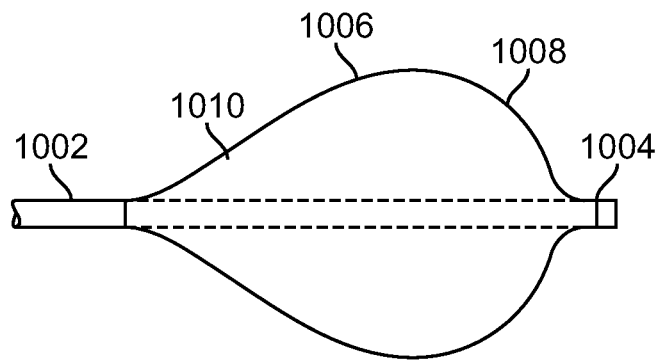
FIGS. 15-20 show still other exemplary embodiments of a distraction balloon.
Figure 16:
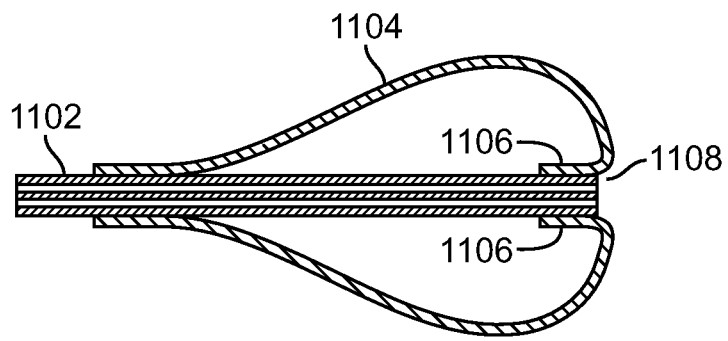
Figure 17:
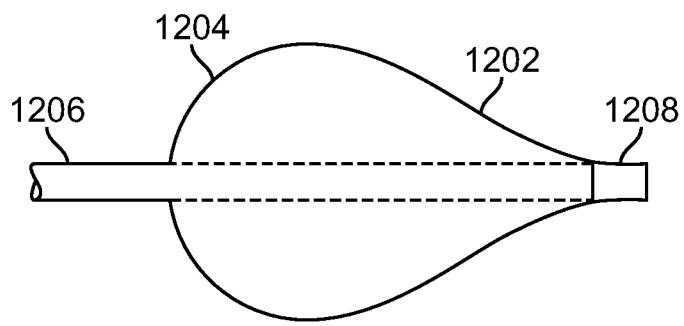

FIG. 15 illustrates another exemplary embodiment of a distraction balloon. The balloon 1006 is asymmetrically tapered and has an almond or teardrop shape. The balloon may have a distal taper 1008 that is different than the proximal taper 1010. In preferred embodiments, the proximal end of the balloon has a shallower taper and the distal end has a steeper taper. The distal end of the balloon may also be rounded and convex when inflated as shown in FIG. 16. This shape helps seat the balloon in the fossa. The shallower proximal taper is preferably in the range of about 10 to 45 degrees while the distal taper is preferably in the range of about 30 to 90 degrees. The shaft 1002 and the distal tip 1004 may include any of the features disclosed in this specification. FIG. 16 illustrates another embodiment of a distraction balloon having a convex distal end. In FIG. 16, the distal balloon walls 1104 are everted into the balloon and the exterior surface of the balloon is attached to the shaft 1102 thereby forming a convex distal region 1108 on the balloon when inflated. One advantage of this configuration is that it eliminates the distal taper on the balloon so that the working surface of the balloon which engages the joint surfaces is very close to the distal tip of the catheter without needing extra length to accommodate a distal taper. Optionally, any of the distal tip or shaft features disclosed herein could easily be used with this balloon configuration. In still other embodiments, the proximal and distal tapers may be reversed. For example, FIG. 17 illustrates an embodiment where the distal taper 1202 is shallower than the proximal taper 1204. The balloon is mounted to shaft 1206 having distal tip 1208 which may be any of the tips disclosed herein. The ranges of the proximal and distal taper are similar to those disclosed above, but they are reversed. This embodiment may have the advantage that as the balloon inflates it may tend to push itself distally until the proximal portion with the largest diameter is seated in the fossa. This leaves the anterior portion of the joint unoccupied by the balloon so as to provide maximum space for visualization and instrument access.

Figure 18:
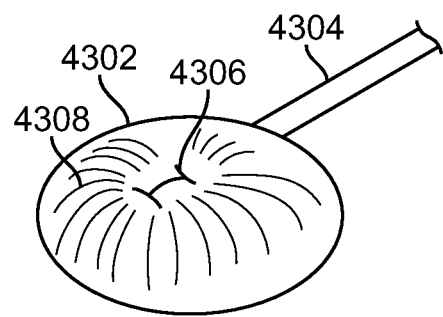
Figure 19:
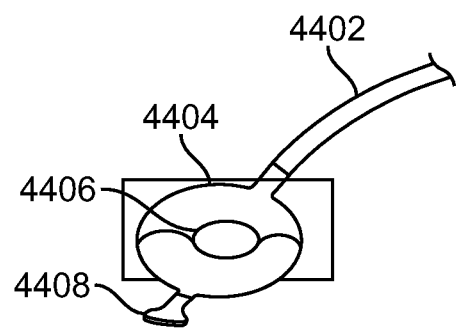
Figure 20:
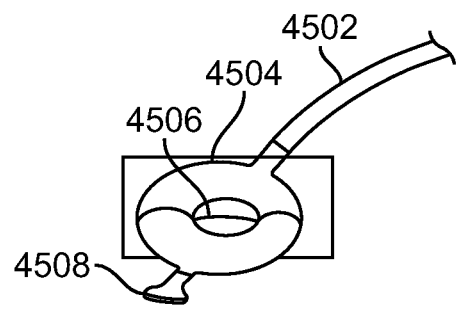

FIG. 18 illustrates a donut shaped balloon 4302 coupled to the distal portion of a shaft 4304. The central depressed region 4306 of the donut is advantageous because it provides an even contact surface for distributing forces and seating of the femoral head which helps to stabilize the balloon in the joint space. Additionally, the outer convex surface 4308 of the donut similarly provides a ring of contact to distribute forces and help stabilize the upper surface against the acetabulum. FIG. 19 illustrates an embodiment similar to that of FIG. 18, except that the balloon 4404 is shaped like a life preserver or ring buoy and has an aperture 4406 extending all the way through the central portion of the balloon. The balloon 4404 is coupled to shaft 4402 and the distal tip 4408 is flared outwardly and flattened to provide a wide and thin leading edge to facilitate advancement through the joint space. FIG. 20 also illustrates a life preserver or ring buoy shaped balloon 4504 attached to a shaft 4502. This embodiment includes a webbed region 4506 within the center of the balloon. The distal tip 4508 is also a flattened flared region. The webbed region 4506 allows an articular surface to be isolated from the remainder of the joint and thus polymeric material may be delivered thereto and polymerized by light or heat or other means in order to help repair the surface. Alternatively, a bioactive material such as chondrocytes, mesenchymal stem cells, growth factors, etc. or other therapeutic agents may be delivered to the isolated region to stimulate healing.

Figure 21A:
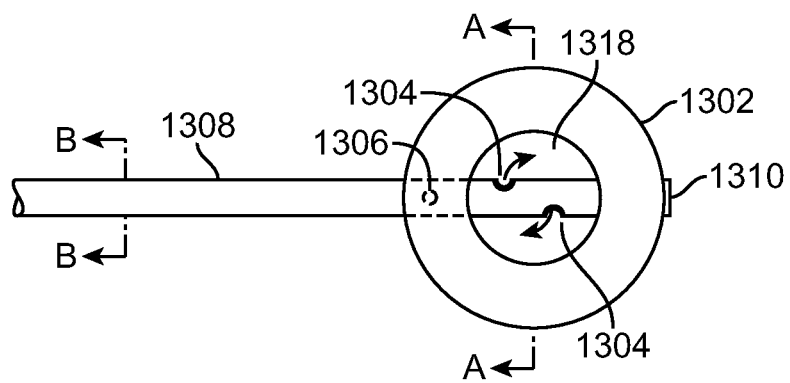
FIGS. 21A-21C illustrate yet another exemplary embodiment of a distraction balloon.
Figure 21B:
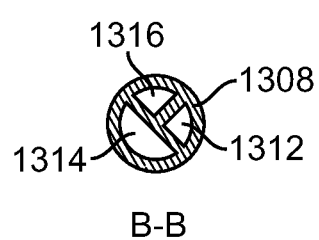
Figure 21C:
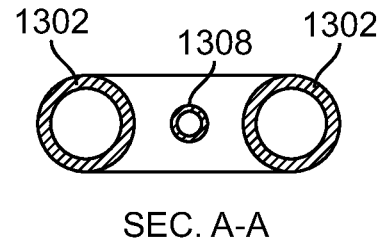

Some balloon embodiments not only distract the joint, but also isolate portions of the joint to create a dry field which facilitates visualization or repair of tissue. For example, FIG. 21A illustrates a toroidal or donut shaped balloon 1302 that can encircle an open central area. When the balloon is inflated in the joint, the upper and lower balloon surfaces engage and seal the surfaces of the joint such that the central region 1318 is fluidly isolated from the remainder of the joint. The toroidal shaped balloon 1302 is preferably attached to the shaft 1308 in such a way as to facilitate introduction of instruments, therapeutic agents or other materials into the isolated area 1318 while the balloon is inflated. For example, the balloon 1302 may be attached to shaft 1308 such that the central axis of the toroid is perpendicular to the longitudinal axis of the shaft (similar to a candy lollipop) and the shaft 1308 may extend across the width of the balloon with a distal atraumatic tip 1310. The shaft 1308 has multiple lumens and distal ports 1304 in the isolated area 1318 through which devices, fluids, or other materials may be introduced into the isolated area. At least one lumen is used to inflate the balloon 1302 through an inflation port 1306. FIG. 21B illustrates a cross-section of shaft 1308 taken along the line B-B in FIG. 21A and shows three lumens 1312, 1314, 1316 which may be coupled with the inflation port 1306 and the other ports 1304. FIG. 21C illustrates a cross-section of the balloon 1320 taken along line A-A in FIG. 21A.

FIG. 22A illustrates an alternative embodiment of a distraction balloon that isolates a region of the joint and provides a barrier against fluid entry. In FIG. 22A, a similar toroidal or donut shaped balloon 1402 is attached to a shaft 1410. However, in this embodiment, the distal end of the shaft is coupled to the balloon such that a distal port 1406 is disposed in the isolated region 1404 of the balloon (the center of the toroid). Thus, fluids, instruments or other materials may be deployed from the catheter shaft tip into the isolated region. Shaft 1410 may have multiple lumens, one lumen 1414 for balloon inflation with an inflation port 1408 that exits the shaft under the balloon and at least a second larger lumen 1412 for passage of the instruments or other materials. FIG. 22B illustrates a cross-section of shaft 1410 taken along the line A-A in FIG. 22A. An additional advantage of this embodiment is that the distal shaft tip is protected by the balloon and therefore the shaft is less likely to cause tissue damage during delivery of the shaft into the joint space.

Figure 25A:
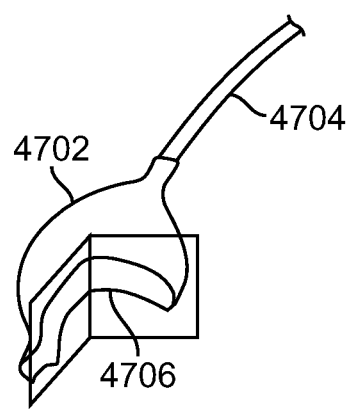
Figure 25B:
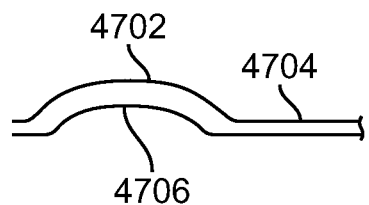

An alternative embodiment of a distraction balloon may have a dome shape in order to create an isolated hollow space surrounded by the dome when the balloon is inflated. FIG. 23A shows the dome shaped balloon 1502 coupled to shaft 1502. Instruments, fluids or other materials may be delivered from the distal port 1510 of shaft 1502 into the hollow space 1506 within the dome. Shaft 1502 also has an inflation lumen with inflation port 1508 fluidly coupled with the balloon 1504 to allow inflation thereof. FIG. 23B shows a cross-section of the distraction balloon taken along the line A-A in FIG. 23A. The upper surface of the dome may also be shaped to match the contour of the fossa, thus when inflated, the dome conforms to the fossa, helping to stabilize the balloon in the joint space. FIGS. 25A-25B illustrate another embodiment of a dome-shaped distraction balloon. Balloon 4702 is shaped like a bell or dome having a concave region 4706. FIG. 25A illustrates a perspective view of the balloon 4702 and FIG. 25B shows a midline section view of FIG. 25A.

Figure 24:
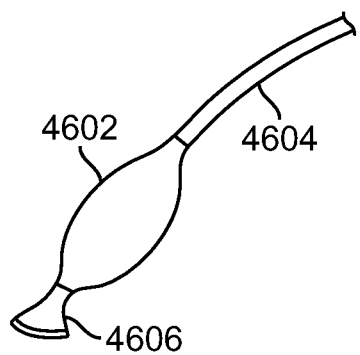

FIG. 24 illustrates yet another embodiment of a distraction balloon. Balloon 4602 is ellipsoidal or oval-shaped and is coupled to shaft 4604 and optionally has a flat flared tip 4606. The ellipsoidal balloon may be symmetrically shaped about the longitudinal axis of the catheter shaft, or it may be flatter on the upper or lower surface.

Figure 26A:
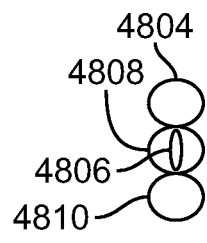
Figure 26B:
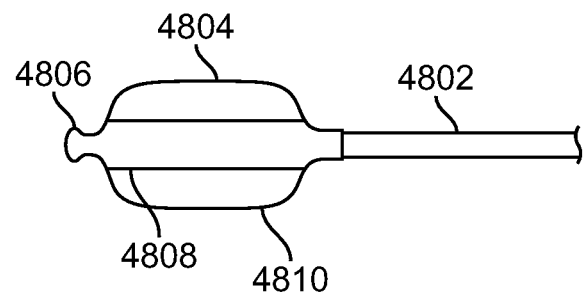

FIGS. 26A-26B illustrate a multi-element balloon distraction device having three expandable balloons. An upper balloon 4804, a middle balloon 4808 and a bottom balloon 4810 are coupled to shaft 4802. Various tips 4806 such as a flat flared tip may be placed on the distal end of the device or any other the other tips disclosed herein may be used. Each of the balloons 4804, 4808, 4810 may be inflated independently of one another or simultaneously. Additionally, each balloon may have a unique shape or size from the other balloons, or they may all be the same size. The balloons may be made from the same material or each balloon may be made from a different material to provide variable material properties. Having multiple balloons on the device allows the balloons to be independently inflated to fit the joint space and optimize the direction of distraction, and also has the added benefit of still maintaining joint distraction even if one of the balloons bursts. FIG. 26A is an end view of the multiple balloon device and FIG. 26B is a side view. Additionally, multiple balloons on the device allow the joint to be distracted varying amounts and at different locations in the joint to distract the joint in different directions.

In still another embodiment of a balloon distraction device, FIGS. 27A-27C illustrate a forked balloon. In FIG. 27A, the opposable balloon elements 4904, 4906 biased outwardly away from each other and are constrained by an outer shaft 4902. The outer shaft 4902 is retracted in FIG. 27B to expose the opposable balloons 4904, 4906 and in FIG. 27C both opposable balloon elements 4904, 4906 are expanded. The balloons may be connected to a common inflation lumen or to independent inflation lumens. The forked embodiment allows the device to be inserted into a joint space such as the hip each of the balloons 4904, 4906 may be placed on opposite sides of the ligamentum teres to provide a distraction force on both sides of the ligamentum teres.

FIGS. 28A-28B illustrate another embodiment of a distraction device. An elongate, sausage shaped balloon 5002 is coupled to a shaft 5004 having an actuation mechanism 5006, as shown in FIG. 28A. Actuating the actuation mechanism 5006, here by retracting a cable coupled with the distal end of the shaft, causes the balloon 5002 and shaft to curl up into a toroidal or semi-toroidal shape as seen in FIG. 28B. The actuation mechanism may then be locked in place to maintain the toroidal shape in use. Alternative embodiments will have a coupling mechanism on the tip of the shaft (not illustrated) that releasably couples with the shaft proximal to the balloon when in the toroidal configuration.

One of skill in the art will recognize that any of the balloon embodiments may include radiopaque markers on the balloon or the shaft to help with visualization during a distraction procedure. It will also be appreciated that other balloon shapes may be used for joint distraction and therefore the present invention is not limited to the exemplary embodiments disclosed herein.

Figure 29A:
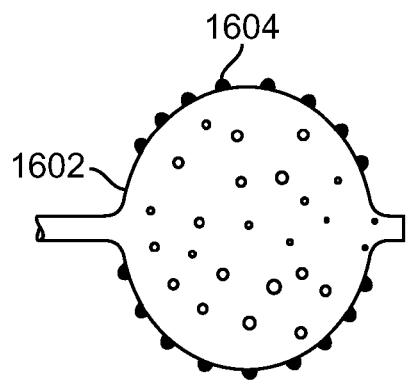
FIGS. 29A-29C illustrate various surface features on a distraction balloon.
Figure 29B:
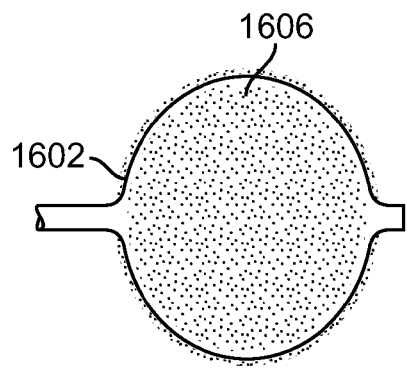
Figure 29C:
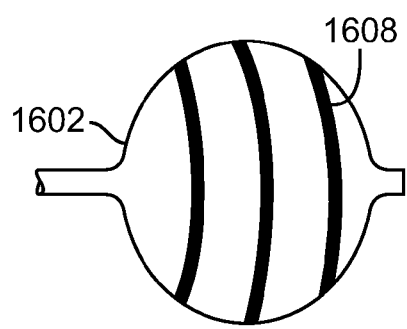

In addition to using balloon geometry to help the balloon seat in the fossa space, balloon surface coatings and features may also be employed. For example, surface features such as bumps, projections, or ridges may be added to one facet or multiple facets including opposing upper and lower facets or on all surfaces of the balloon. For example, in FIG. 29A, balloon 1602 includes bumps 1604 on the outer surface, while in FIG. 29B the outer balloon surface 1602 has been textured 1606, and in FIG. 29C, ridges 1608 have been added to the outer surface of the balloon 1602. Additionally, the outer balloon surface may be coated with a sticky layer of material to help it remain in the joint space. Any of these features may be used in combination with any of the balloon embodiments disclosed herein.

Figure 30:
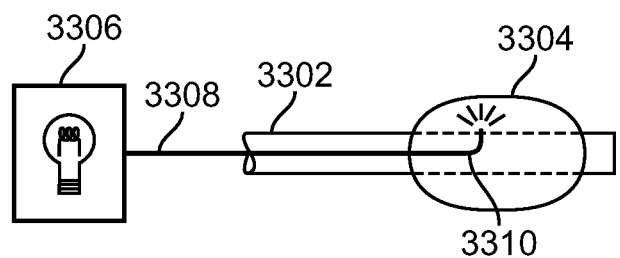
FIG. 30 illustrates an optional fiber optic light source in combination with a balloon distraction catheter.
Figure 31:
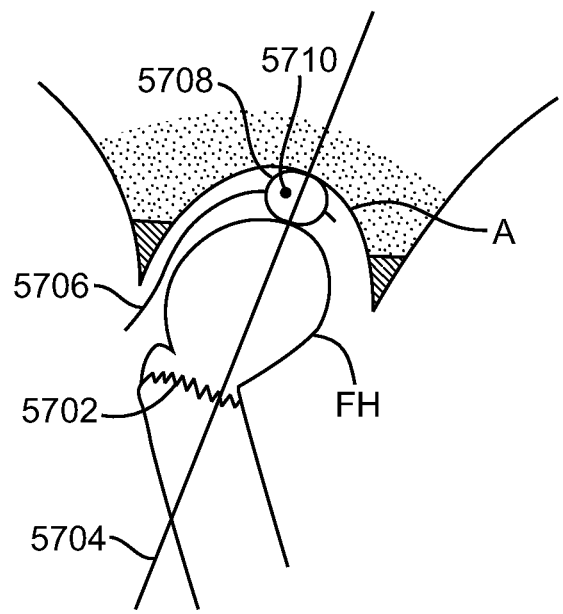
FIG. 31 illustrates a sensor in the distraction balloon.

It may also be important for a physician to be able to see through the balloon and be able to view regions of the joint behind the balloon, typically using an arthroscope. The balloon therefore will preferably be inflated with an inflation fluid which is translucent. Furthermore, the balloon may be constructed of materials which have a refractive index approximately the same as that of the inflation fluid and/or that of the fluid in the joint space. The balloon may also be coated with a material that reduces reflection and enhances translucency. The shaft of the balloon catheter may also include a fiber optic or other light source at its distal end to allow lighting of the joint space. The light source may be within the interior of the balloon, or may be external to the balloon, either proximal or distal to the balloon. FIG. 30 schematically illustrates an exemplary embodiment of a balloon 3304 attached to a catheter shaft 3302. A fiber optic 3308 extending through shaft 3302 delivers light from a light source 3306 external to the patient, which may be a laser, LED, or other suitable light source, to the balloon interior 3310 where the light is emitted to illuminate the joint. The balloon or the shaft may also have other features to facilitate joint repair. For example, in FIG. 31 a femoral head FH has fractured 5702 away from the rest of the femur. Physicians typically repair this type of fracture by drilling a hole and inserting a screw or rod along the line 5704 through the femur into the femoral head. If the hole or the screw or rod are advanced too far into the bone, the drill bit or the screw or rod could protrude from the femoral head damaging the surface of the acetabulum or other adjacent tissues. Thus, a balloon 5708 mounted on a shaft 5706 and having a sensor 5710 within the balloon or near the distal end of the shaft may be used to detect when the drill or the rod or screw is about to penetrate the femoral head. The sensor 5710 may be an ultrasound, infrared, magnetic, capacitance, or suitable sensor. Alternatively an ultrasonic imaging device may be mounted to the shaft 5706 in or near balloon 5708 to enable ultrasonic imaging of the joint space or surrounding tissues.

Figure 32A:
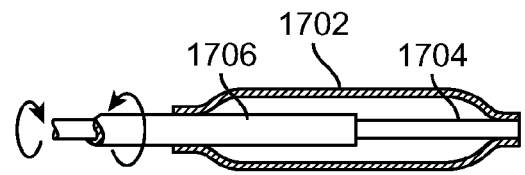
FIGS. 32A-32C illustrate various embodiments of low profile distraction balloons.
Figure 32B:
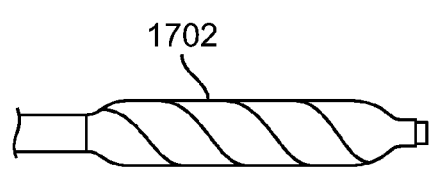
Figure 32C:
Figure 33:
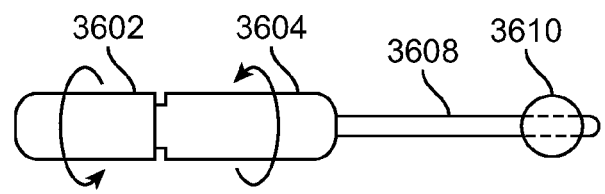
FIG. 33 illustrates an actuator mechanism.

Balloon profile is also important during delivery and during removal from the joint. Because the joint space is particularly tight before distraction, it is desirable to provide a balloon with the lowest delivery profile possible. The balloon may be shaped and have pleats, folds, or other features to help it collapse to a minimal profile upon deflation to facilitate introduction and withdrawal. In addition to carefully folding the balloon over the shaft and delivering the balloon sheathed, other mechanisms may be employed to help maintain a low profile. The proximal and distal ends of the balloon may be coated with a lubricious low-friction coating to facilitate retraction of the balloon into a cannula, sheath or other access device. Other mechanisms actively collapse the balloon. For example, in FIG. 32A, the catheter includes an inner shaft 1704 and an outer shaft 1706 disposed over the inner shaft 1704 and rotatable relative thereto. The distal end of the balloon 1702 is attached to the inner shaft 1704 and the proximal end of the balloon 1702 is attached to the outer shaft 1706. Rotation of the outer shaft relative to the inner shaft twists balloon 1702 as seen in FIG. 32B. Thus balloon 1702 is tightly and helically wrapped around the shafts as shown in FIG. 32C resulting in a minimum profile. Additionally, the twisting motion helps evacuate substantially all of the inflation fluid from the balloon, further reducing the deflated profile. An actuator mechanism may be included on the proximal end of the shafts that can be actuated by a physician to perform the shaft rotation. FIG. 33 illustrates an exemplary actuator mechanism. In FIG. 33, a proximal handle has two sections 3602 and 3604. One section is operably coupled with the inner shaft and the other section is operably coupled with the outer shaft. Rotation of one section relative to the other will result in rotational along the shaft and wrapping of the balloon 3610.

Figure 34:
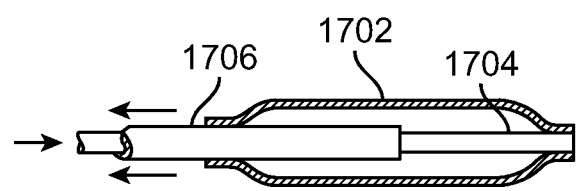
FIG. 34 illustrates another embodiment of a low profile distraction balloon.
Figure 35:
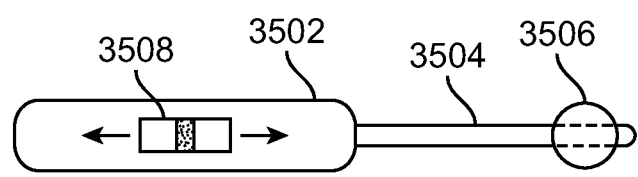
FIG. 35 illustrates another actuator mechanism.

FIG. 34 illustrates an alternative embodiment where instead of rotating the inner shaft relative to the outer shaft, the inner shaft 1704 is slidable distally relative to outer shaft 1706 such that the proximal and distal ends of the balloon may be separated to apply tension to the balloon 1702. Again, the shafts may be controlled with an actuator mechanism on the proximal end of the inner and outer shafts. This stretches the balloon longitudinally so as to minimize balloon profile. FIG. 35 illustrates an exemplary actuator mechanism on a proximal handle 3502. Movement of slide 3508 will result in relative movement of the outer shaft 3608 with respect to the inner shaft, resulting in the desired tension in balloon 3506. Thus linear movement or rotation of the shaft can be used to actively collapse the balloon.

Figure 36:
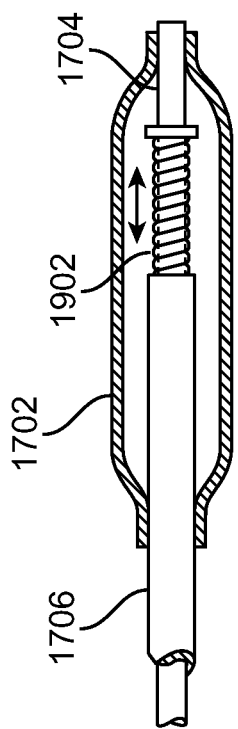
FIG. 36 illustrates another embodiment of a low profile distraction balloon.

FIG. 36 illustrates still another embodiment where the balloon is linearly stretched. In FIG. 36, a compression spring 1902 is disposed between the inner 1704 and outer shafts 1706. The spring 1902 is biased in an elongated configuration so that the inner shaft is biased to move distally relative to the outer shaft, again stretching balloon 1702 and reducing its profile. Upon inflation of the balloon, the balloon radially expands and this force is high enough to overcome the spring force and retract the inner shaft 1704 relative to the outer shaft 1706 thereby permitting balloon expansion. Additional details on similar mechanisms are disclosed in U.S. Pat. No. 7,488,337 to Saab which is incorporated herein by reference. In other embodiments, instead of a linear spring, a torsional spring may be used. In addition, the balloon may be attached to the shaft so as to be normally in torsion or in tension when deflated so that it preferentially exists in a collapsed configuration which is overcome during inflation. Upon deflation, the balloon returns to its collapsed configuration.

Figure 37B:
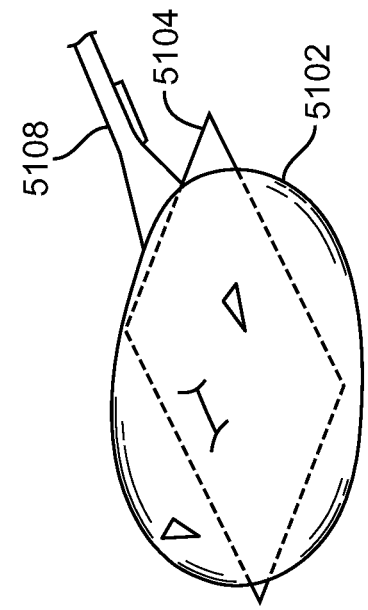
FIGS. 37A-37B illustrate yet another embodiment of a low profile distraction balloon.
Figure 37A:
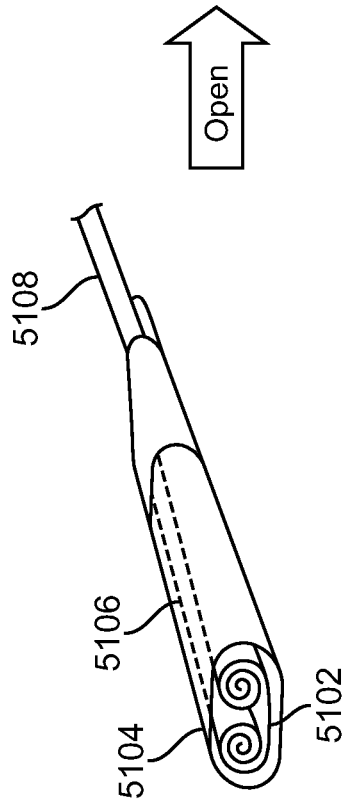

A deflated balloon may also be constrained by rolling it into a low profile configuration and constraining it with a sheath. The sheath may be retracted after the balloon has been delivered to a target site and the balloon may be expanded. FIGS. 37A-37B illustrate an alternative embodiment where the constraining sheath 5104 is perforated along line 5106. A shaft 5108 carries the balloon 5102 which is maintained in a rolled up, low profile configuration by sheath 5104. Once the balloon is delivered to the target site, it is inflated. Inflation of the balloon 5102 forces the sheath to tear along the perforation 5106, allowing the balloon to fully expand as seen in FIG. 37B.

Figure 41:
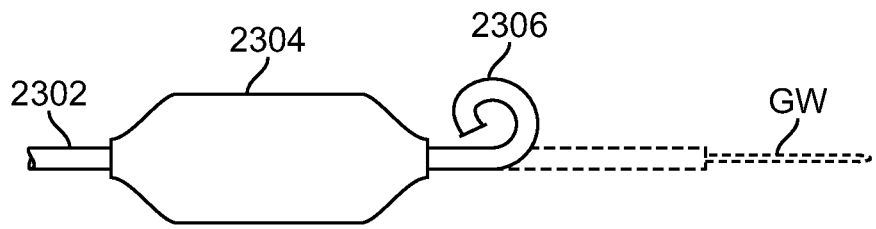
FIGS. 41, 42A-42B and 43 illustrate other distraction balloon tips.
Figures 42A, 42B:
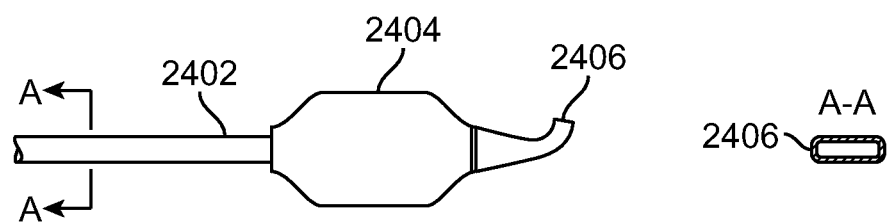

Catheter tip configurations are also an important feature of the balloon catheter. The tip should be configured so that it can be passed into and through the joint without getting hung up or damaging joint tissue and bone structures. In particular, the tip should be adapted to pass through the joint without the tendency to go into the fossa where it may engage the fossa walls or ligamentum teres and become obstructed from further advancement. The tip should also be adapted to allow the entire balloon to enter the joint and to be seated in the fossa without undesirable engagement with the posterior articular joint surfaces. The tip will preferably be flexible, usually more flexible than the rest of the catheter shaft. Also, the tip is preferably resilient so that when it has a pre-defined shape, the tip will return to this unbiased shape. Thus the tip preferably extends no more than 10 mm, and more preferably no more than about 5 mm, beyond the distal end of the balloon when the tip is straightened. FIG. 38A illustrates a straight tip 2004 on the end of shaft 2006 having a balloon 2002. FIG. 38B illustrates a cross-section of the tip 2004 taken along the line A-A in FIG. 38A. FIG. 39A illustrates a tapered or conical tip 2102. FIG. 39B illustrates a cross-section of tip 2102 taken along line A-A in FIG. 39A. In some embodiments, the tip may be tapered only on two opposing sides so it more readily bends about a preferred transverse axis. FIG. 39C illustrates a cross-section taken along line A-A in FIG. 39A when the tip includes a taper only on two opposing sides 2104 so that it more easily bends about a vertical transverse axis than about other transverse axes. FIG. 40A illustrates another embodiment having a spherical or bullet shaped tip 2202 with a blunt atraumatic distal tip and FIG. 40B illustrates a cross-section taken along line A-A in FIG. 40A. In other embodiments, the tip may have a curve, J-shape, or pigtail shaped. FIG. 41 illustrates a balloon 2304 coupled to a shaft 2302 having a pigtail tip 2306. The pigtail 2306 may be straightened out by passing the catheter over a guidewire GW extending through a lumen in the tip, or a stylet may be positioned in a lumen of the shaft and tip. FIG. 42A illustrates a tip 2406 having a slight curve in it. Additionally, the shaft 2402 has a cross-sectional width greater than its cross-sectional height, as seen in FIG. 42B which is a cross-section taken along line A-A in FIG. 42A. This configuration preferentially allows the shaft to bend transverse to the width since the upper and lower sections are less stiff than the side sections. The tip 2406 is optionally pre-curved about an axis parallel to that about which shaft 2402 bends more easily. With this structure the device is adapted to pass through the curved space between the ball and socket of a joint with minimal engagement with the joint surfaces. Balloon 2404 is attached to shaft 2402 which may have the same cross-sectional profile or another profile such as round, square, rectangular, oval or any other profile. Any of these tip configurations described above may be combined with any of the other balloon embodiments or other features disclosed herein.

Figure 43:
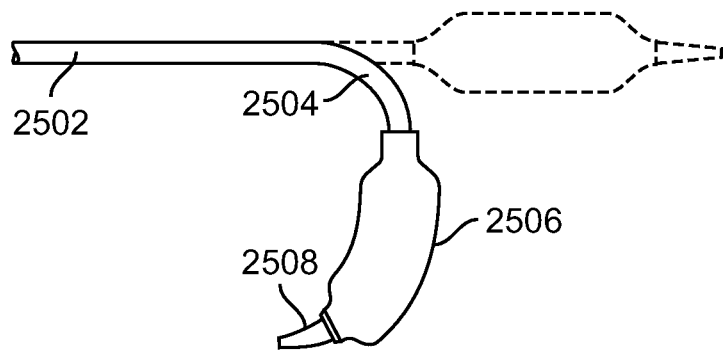

In addition to various cross-sectional geometries, the catheter shaft itself may have features which will facilitate its introduction into the joint space. In particular, the hip joint is challenging due to its curvature and depth and surrounding tissue, including ligaments, and tendons that must be penetrated. In one exemplary embodiment, the shaft may have a precurved shape to facilitate such introduction. FIG. 43 illustrates a balloon 2506 attached to a shaft 2502 having a precurved region 2504 and a tapered distal tip 2508. The shape of the curve region 2504 depends on the desired access location relative to the position in the joint where the balloon is to be placed, such as the fossa in a hip joint. In FIG. 43, a distal section of the shaft approximately 25 to 50 mm from the distal end has a curve with a radius approximately the same as the radius of curvature of the acetabular socket. The radius preferably substantially matches that of the socket, but may vary by plus or minus 20%. Additionally, in this embodiment, a stylet may be removably positioned in a lumen of the shaft 2502 in order to temporarily straighten out the curved portion during delivery, as illustrated in phantom in FIG. 43.

Figure 44A:
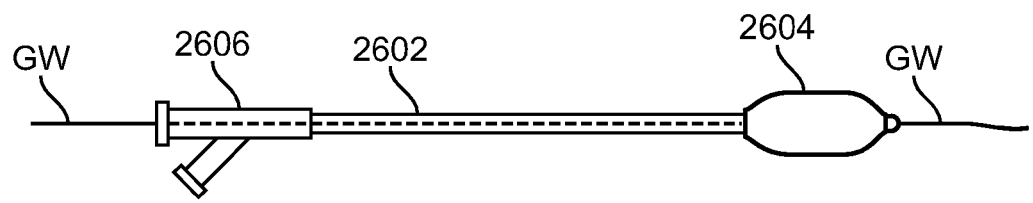
FIGS. 44A-44C illustrate several embodiments showing use of a guidewire with a distraction balloon.
Figure 44B:
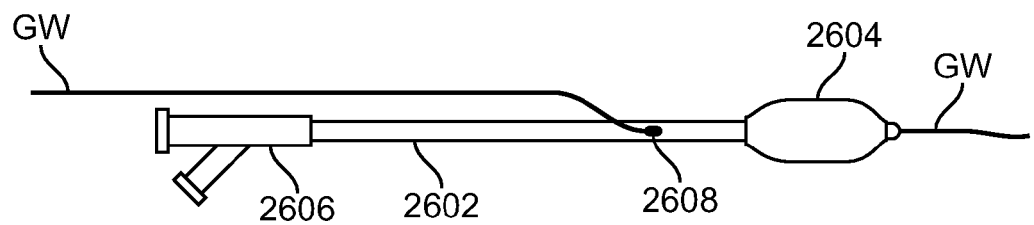

The shaft will usually have a lumen for inflation of the balloon. Additionally, the shaft may have a guidewire lumen so that the shaft may be advanced over a guidewire into the joint. The guidewire lumen may extend the full length of the catheter shaft or an exit port may be provided between the balloon and the proximal end of the catheter, usually in the distal half of the catheter, to allow easier placement of the catheter over the wire. For example, FIG. 44A illustrates a conventional over-the-wire configuration where the shaft 2602 has an inflation lumen and a guidewire lumen extending the entire length of the shaft. The guidewire GW exits from a distal port on the catheter tip. The guidewire passes through the interior of balloon 2604 on the distal end and through a connector hub 2606 on the proximal end. FIG. 44B illustrates an embodiment where the guidewire exits a port 2608 that is closer to the balloon 2604 and the distal end than it is to the proximal catheter end. This configuration is sometimes referred to as rapid exchange.

Figure 44C:
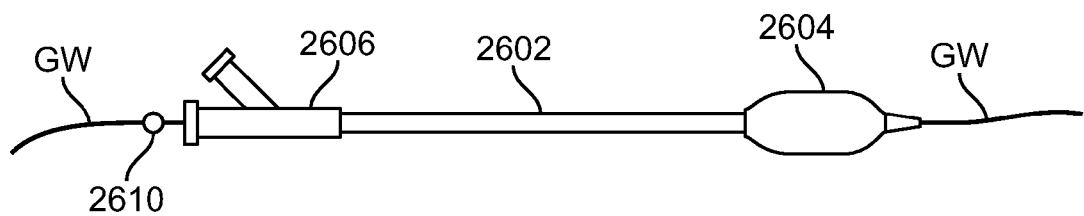

A stopping element may also be coupled with the guidewire in order to prevent over-extension of the guidewire beyond the distal tip of the shaft to a point where the guidewire could damage joint tissues distal to the shaft and balloon. In FIG. 44C, stopping element 2610 is an elastomeric or metallic ball frictionally fit over or otherwise attached to the guidewire GW. It could also be a collet or other device that can be attached to the guidewire a predetermined distance from the wire's distal end and that has a size larger than the guidewire lumen so that it cannot pass into the guidewire lumen. The stopping element is preferably detachable from the guidewire with a set screw or other reversible clamping means to secure it to the wire at the desired position.

Figure 45A:
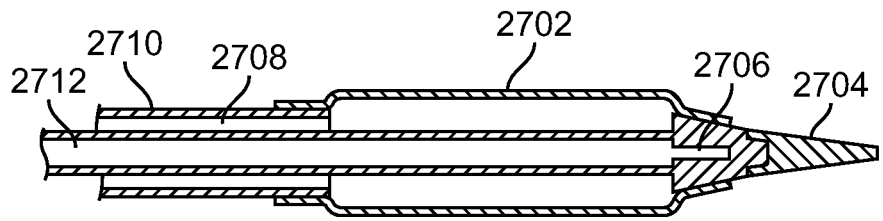
FIGS. 45A-45C illustrate use of a stylet.
Figure 45B:
Figure 45C:
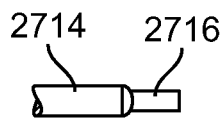
Figure 45D:
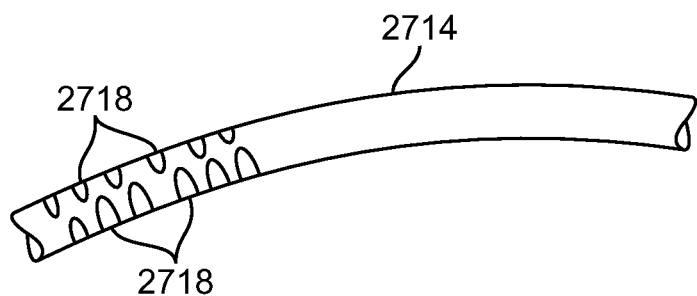
FIG. 45D illustrates a slotted shaft.

The shaft may also have a lumen to receive a stylet for supporting the shaft and enhancing its column strength. The lumen could be a shared lumen, e.g. shared with the guidewire lumen or the inflation lumen, or the catheter may have a separate stylet lumen. The lumens may be coaxial with one another or parallel. For example, FIG. 45A illustrates a balloon 2702 attached to a catheter shaft 2710 having a balloon inflation lumen 2708 and a stylet lumen 2712. The stylet lumen 2712 extends into a garage or pocket 2706 in the distal tip 2704 of the catheter. Thus, the stylet may be advanced until it bottoms out in the pocket 2706. The stylet may have a round cross-section or it may be rectangular or oval so that it bends preferentially about one axis. Additionally, the distal tip of the stylet may be keyed to the pocket 2706 so that the two are releasably coupled together and rotatably interlocked. For example, a stylet 2714 may have a flat distal section 2716 which fits in pocket 2706. This allows the stylet to be rotated which will also correspondingly rotate the distal catheter tip. This allows the distal end of the balloon to be twisted relative to its proximal end when deflated so as to helically wrap the balloon, minimizing profile. FIG. 45C illustrates the tip of stylet 2714 having a keyed tip 2716. In this embodiment, the tip 2716 is flat like a screwdriver, but one of skill in the art will appreciate that many other tip geometries may be employed, such as a square or cross shape to fit into a pocket of complementary shape. The stylet will have sufficient flexibility to allow deflection into a curved configuration as the catheter is inserted and advanced into the joint space. In addition to straight stylets, the stylet may also be pre-shaped into a curve to facilitate introduction. The stylet may also include a series of parallel transverse cuts or slots 2718 along a portion of its length to enhance bending in one or more directions, as illustrated in FIG. 45D. The slots may be symmetrically arranged on four opposing sides of the stylet so that the stylet bends symmetrically in the four directions or the slots may be located on only one side or two opposing sides so that the stylet bends more easily about one axis or in one or more directions.

Figure 46A:
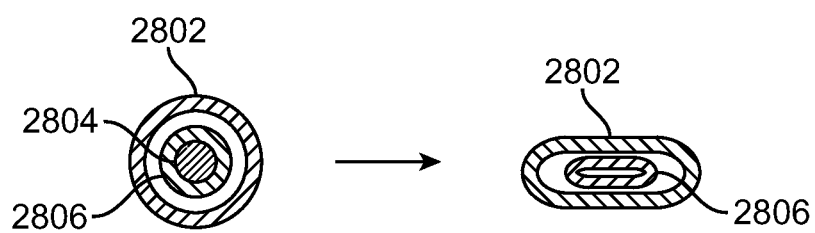
FIGS. 46A-46B illustrate various shaft configurations.
Figure 46B:
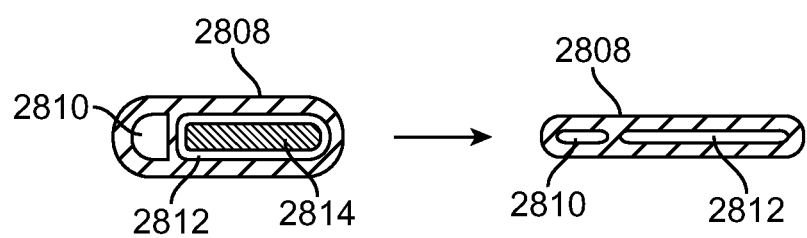

The shaft may also be configured to collapse to a flat configuration when the lumens are evacuated, minimizing its profile and the space that it occupies in the joint. This allows the shaft to be flattened when the balloon is deflated so as to minimize any distraction of the joint or interference with joint movement, allowing the physician to leave the balloon in place and manipulate the joint. For example, in FIG. 46A, shaft 2802 has a round profile when an inner lumen 2806 is filled with a stylet 2804, inflation fluid or a guidewire. Once the stylet 2804 is removed, the shaft collapses into an oval or flattened shape. FIG. 46B illustrates another embodiment wherein the shaft 2808 has two lumens 2810 and 2812. When stylet 2814 is positioned in lumen 2812, the shaft takes its expanded oval or rectangular cross-sectional shape and when stylet 2814 is removed, the shaft 2808 takes a flattened oval or rectangular form of substantially reduced cross-sectional height. Preferably the cross-sectional height of the shaft when collapsed will be less than about one half and more preferably less than about one third the cross-sectional height when not collapsed. An additional advantage of the rectangular shaped shaft 2808 and correspondingly shaped stylet 2804 of FIG. 46B is that its cross sectional geometry allows it to more easily bend around one transverse axis than around others. This is due to the fact that the shaft width along one axis transverse to the shaft is substantially greater than the shaft height along a second transverse axis orthogonal to the first axis. In preferred embodiments, the cross-sectional width is at least about 1.5 to 5 times the shaft cross-sectional height. In addition to shafts with oval cross-section, shafts with rectangular, racetrack, and other asymmetrical cross-sections may also be used.

Figure 47A:
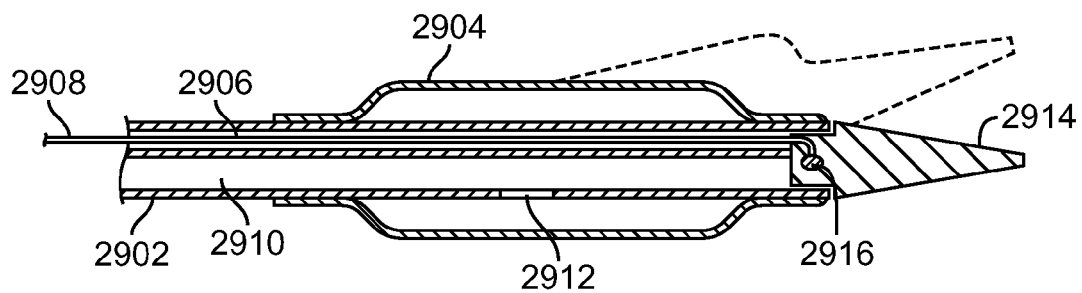
FIGS. 47A-47B illustrate deflection of the shaft.
Figure 47B:
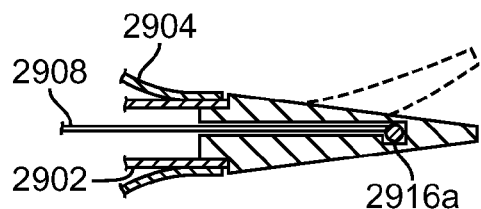

Some catheter embodiments may include steerable features to help direct the catheter as it is being introduced into the joint space. In FIG. 47A a balloon 2904 is attached to a catheter shaft 2902 having a tapered tip 2914. Shaft 2902 has two lumens. A first inflation lumen 2910 is fluidly coupled with the balloon via port 2912 to allow inflation and deflation of the balloon. A second lumen 2906 allows a pullwire 2908 to slidably extend from the proximal end of the catheter to a distal portion of the catheter. The distal end of the pullwire may include a ball or other anchor 2916 to facilitate its attachment to the distal portion. In preferred embodiments, the pullwire 2908 is off-center from the central axis of the shaft 2902 so that when the pullwire is retracted, the distal portion of the shaft will deflect in one direction, as seen in phantom in FIG. 47A, because exerting tension on the wire will deflect the distal portion through a desired degree of bending. Releasing tension in the pullwire will allow the distal portion to return to its unbiased straight shape. FIG. 47B illustrates an embodiment where the pullwire 2908 is attached near the distal end 2916a of the flexible catheter tip 2914 so that only the tip bends when the pullwire is actuated. The proximal end of the shaft may include a handle with an actuator mechanism such as rotatable knobs, a trigger or a slide mechanism so that a physician may easily control actuation of the pullwire. Actuators similar to those illustrated in FIGS. 33 and 35 may be used to move the pullwire.

Figure 48A:
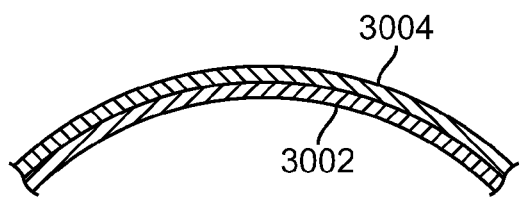
FIGS. 48A-48B and 49A-49B illustrate protection of a distraction balloon.
Figure 48B:
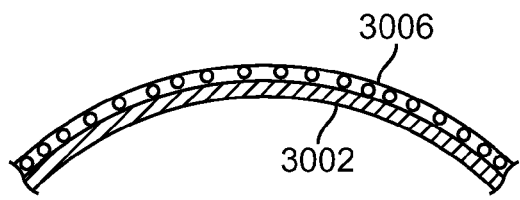

Because the balloon can encounter sharp or rough areas in the joint space and the surgical repair procedure performed on the joint often involves sharp instruments, balloon puncture is a consideration. Therefore, any of the balloons described herein may be multilayered or may be made from a puncture resistant material or they may include coatings which resist puncture. Fibers, a mesh or layers of Kevlar, Vectran or other materials of high toughness may be embedded in or adhered to the wall of the balloon. The balloon may have a multilayered wall to allow higher burst pressures and increase puncture resistance. For example, in FIG. 48A, the balloon has an inner wall 3002 and an outer wall 3004. The outer wall may be the same material as the inner wall and the two bonded together to provide a greater thickness to increase strength and resist puncture. In some embodiments, the layers need not be bonded together and may optionally have a lubricant between the layers. Also, either one or both ends of the outer layer may be unattached to the the catheter shaft thereby allowing the ends to float slightly as the balloon expands, the inflation fluid being contained in the inner layer, which helps reduce stresses. In an exemplary embodiment, the inner and outer walls are each about 0.0004"-0.0010" in thickness. Alternatively the outer wall may be a different, more puncture resistant material. In other embodiments, the inner and outer wall may be unattached to each other or separated by a gap so if one wall is punctured, the remaining wall will still be intact. FIG. 48B illustrates an inner balloon wall 3002 having a separate layer 3006 of a puncture resistant material.

Figure 49A:
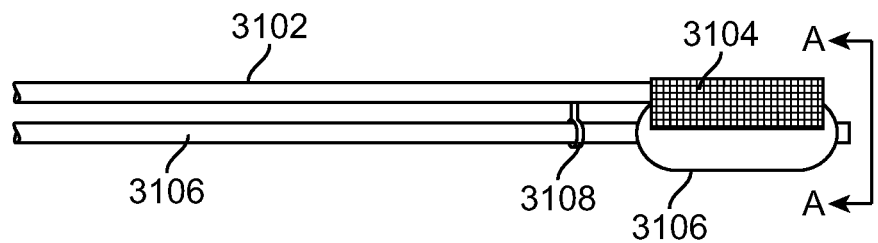
Figure 49B:
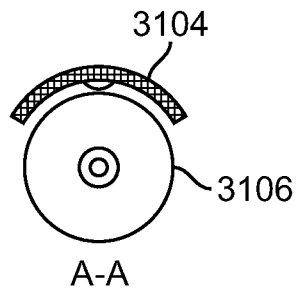

In addition to enhancing balloon puncture resistance, a balloon shield may be used to help protect the balloon from puncture. The shield may be positioned adjacent to or around the balloon and it may be coupled to the balloon catheter shaft or the balloon itself, or it may be part of a separate device independently positionable in the joint. The shield preferably is collapsible by folding or winding, similar to that performed for the balloon, so that the shield may fit in an arthroscopic port or small incision and may be resilient so as to expand once inserted into the port. The shield may also be adapted to connect or adhere to the balloon or catheter shaft to help retain its position. FIG. 49A illustrates an exemplary embodiment of a shield. In FIG. 49A an inflated balloon 3106 is attached to a catheter shaft 3106. Disposed over the balloon is a shield 3104 attached to a shaft 3102. Optionally, the shaft may include an eyelet or clip 3108 which allows the shield to be releasably coupled with the catheter shaft. The shield may have a cylindrical curvature and may be a mesh-like material, a solid metal or plastic, or other material which prevents sharp objects from penetrating the balloon. The shield may be configured to cover only a portion of balloon 3106 or it may encircle the entire circumference of the balloon. FIG. 49B is a cross-section taken along like A-A in FIG. 49A.

Figure 50A:
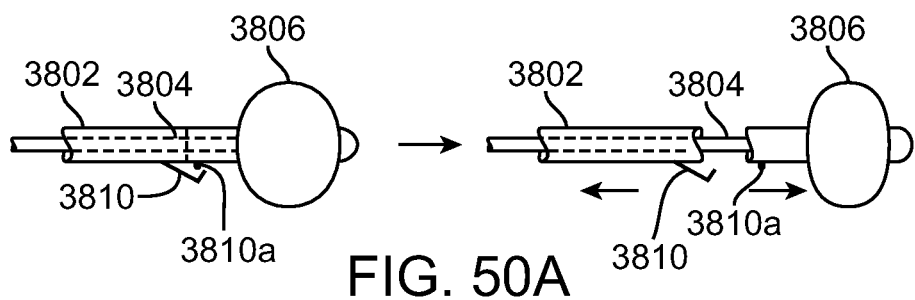
FIGS. 50A-50B illustrate a detachable balloon.
Figure 50B:
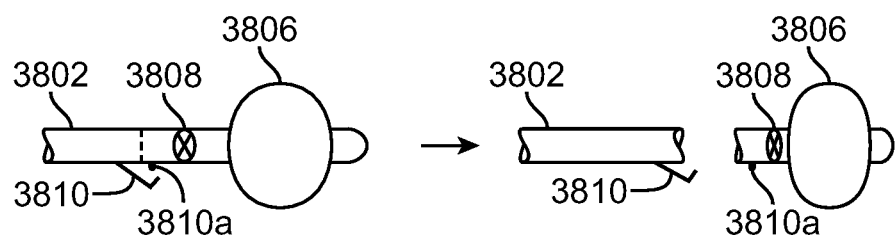
Figure 51A:
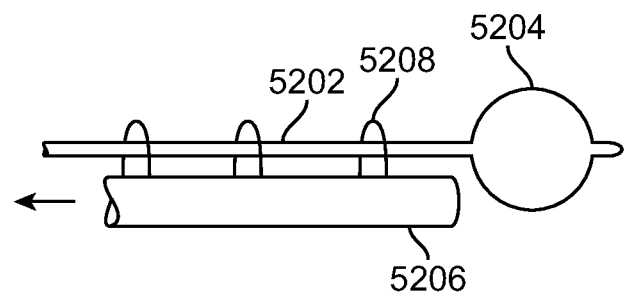
FIG. 51A-51B illustrate another embodiment of a separable balloon.
Figure 51B:
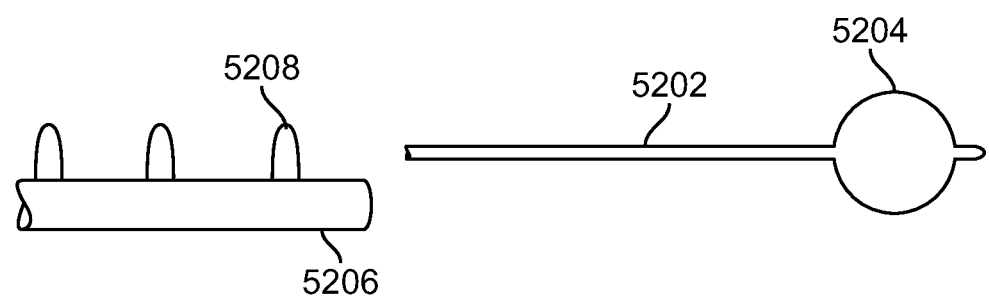

In some embodiments, the balloon may be detachable from the catheter shaft. For example, in FIG. 50A, a balloon 3806 is attached to a shaft 3802. An inflation tube 3804 is disposed in a lumen in shaft 3802. Shaft 3802 has a coupling 3810 on its distal end which releasably couples to a complementary feature 3810a connected to the proximal end of balloon 3806. Once the balloon is inflated in the joint space, the shaft may be decoupled from the balloon either by exerting tension on the shaft or by actuating a mechanism on the proximal end of the device which decouples the coupling 3910, 3910a from the balloon. The inflation tube 3804 remains coupled with the balloon 3806 and the shaft is retracted over the inflation tube. Alternatively the inflation tube may be external and parallel to the shaft 3802. In FIG. 50B, the proximal end of the balloon has a one-way valve 3808 that eliminates the need for an inflation tube. Thus, once inflated, shaft 3802 may be detached from the balloon 3808 and the balloon will remain in the joint space inflated and free of the shaft. FIG. 51A illustrates another embodiment of a balloon distraction device that is detachable from the delivery shaft. A balloon 5204 is coupled to a small, flexible inflation shaft 5202 having an inflation lumen (not illustrated). The inflation shaft 5202 is coupled to a larger diameter and stiffer delivery shaft 5206 by feeding the inflation shaft 5202 through one or more eyelets 5208 on the delivery shaft 5206. Alternatively, the inflation shaft 5202 may be slidably disposed in a lumen of the delivery shaft 5206. One of skill in the art will of course appreciate that other attachment mechanisms may be used to join the inflation shaft 5202 with the delivery shaft 5206. During delivery, the stiffer delivery shaft 5206 is used to help advance the balloon 5204 through the joint space. Once the balloon is advanced to the target site, the outer delivery shaft 5206 may be retracted and withdrawn from the patient, leaving only the balloon 5204 and the inflation shaft 5202 in the joint space. FIG. 51B shows separation of the balloon 3806 from the delivery shaft 5206. This creates maximum space available for other instruments and visualization in the joint space. The balloon may be retracted from the joint space when the procedure is terminated, by simply pulling on the inflation shaft 5202 or by reintroducing delivery shaft 5206 over the inflation shaft to assist balloon removal.

Figure 52:
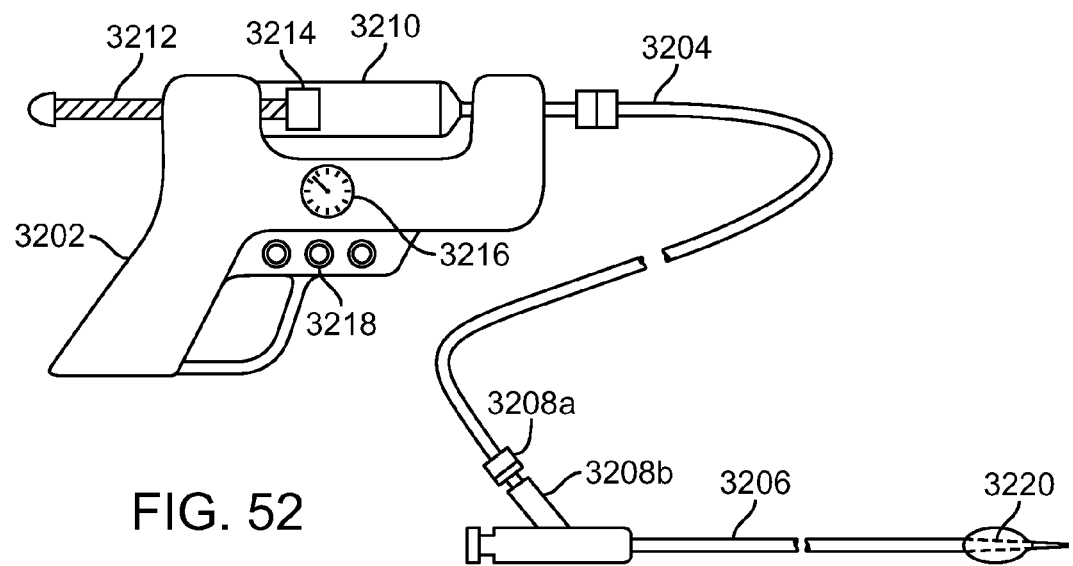
FIG. 52 illustrates a distraction balloon inflator.

In addition to the distraction balloon, a system may include a specialized inflation device such as the exemplary embodiment in FIG. 52. In FIG. 52, inflation device 3202 is fluidly coupled via a flexible tube 3204 to a balloon distraction catheter 3206. The flexible tube 3204 may be releasably coupled to the catheter 3206 using Luer connectors 3208a, 3208b or other common medical device fittings. The inflation device may be designed to be hand held, or to be mounted to an intravenous fluid pole or the operating table, or to be placed on the operating room table or patient's body. For hip distraction, the inflation device should have enough fluid capacity to inflate balloon catheter 3206 with an inflatable volume of at least 16 milliliters to a pressure of 200 psi. The fluid used to inflate the balloon will preferably be sterile saline, sterile contrast media or a combination of both. The inflation device 3202 allows the user to incrementally or fully inflate or deflate the balloon catheter with a push of a button or buttons 3218 and with single handed operation. For example, the inflation device may comprise a fluid cylinder 3210 and a piston 3212 that is driven by an electric motor or hydraulic drive system such that piston 3212 is displaced a known distance for each push of a button 3218. Thus as the piston moves, plunger 3214 displaces a corresponding volume of fluid from the reservoir 3210 to the balloon catheter. One button may allow incremental partial balloon inflation with a set volume of fluid, while a second button inflates the balloon to a fully selected pressure. A third button withdraws all fluid from the balloon by retracting the piston 3212.

Optionally, the inflation device 3212 will include a mechanism which pulls a vacuum on the balloon catheter prior to inflation to remove any air from the catheter. This can be activated by the user with a push of a button or other single handed means. Performing this step ensures that the subsequent inflation will minimize any compressible air present within the catheter and balloon. The "de-airing" mechanism will introduce a bolus of inflation fluid into the balloon to force any air out of the balloon and inflation lumen. The device may be tilted with the balloon downward to allow air to escape proximally through the inflation lumen. A vent may be provided on the inflation device in communication with the inflation lumen to allow the air to escape. The vent may comprise a three-way stopcock on the inflation lumen which may be moved to a position that allows escaping air to exit the inflation lumen. The vent may optionally include a one-way valve to prevent air from re-entering the system.

The inflation device 3202 may also include a gauge 3216 or other type of indicator that indicates balloon pressure and/or amount of distraction. In such embodiments the balloon catheter may include a pressure sensor and/or distraction sensor 3220 on or within the balloon which is electronically coupled to the indicator on the inflation device. The distraction sensor may be an optical sensor such an IR sensor to sense the distance between the joint surfaces and/or the distance to the balloon wall from the shaft. Alternatively the amount of distraction may be simply calculated based on balloon pressure and a pressure/distraction curve created from empirical testing.

Figure 53:
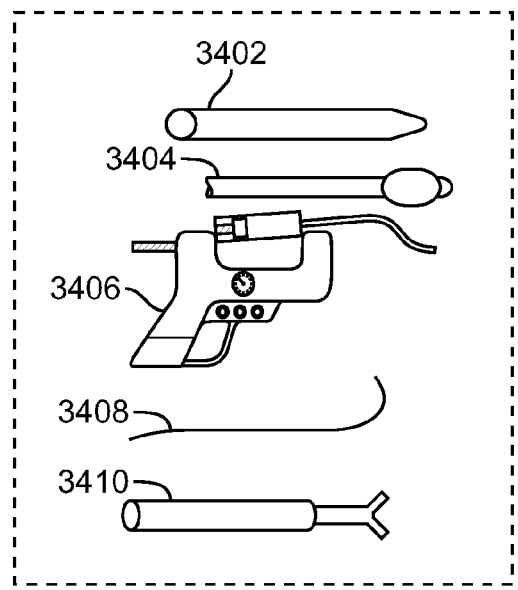
FIG. 53 illustrates a distraction balloon kit.

Other systems may include an internal distraction device in combination with other specialized instruments for performing therapeutic or diagnostic procedures while the joint has been distracted. For example, FIG. 53 illustrates a system which includes an access port or cannula 3402, a balloon distraction catheter 3404, an inflation device 3406, a guidewire 3408 as well as other surgical instruments 3410 including but not limited to fiber optic lights, retractors, cutters, debriders, microfracture awls, suture anchors, suture holders or suture managers. These may be used to arthroscopically view or distend joint tissue. Diagnostic procedures can be performed as well as therapeutic procedures such as debridement, joint flushing or smoothing of joint surfaces and adjacent tissues, and performing other repairs such as that of the labrum. Microfracture of the joint surfaces may also be performed in order to stimulate cartilage or other tissue growth.

Figure 54A:
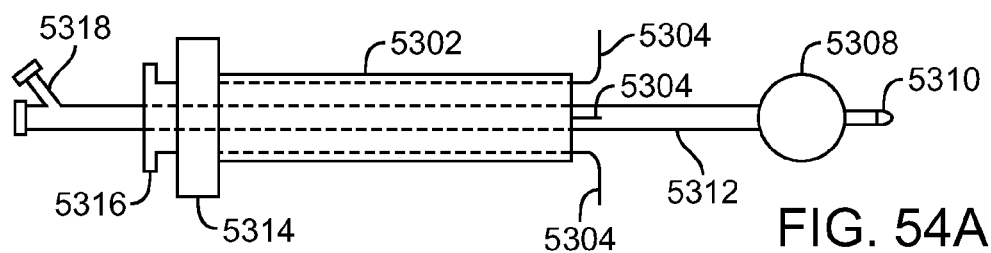
FIG. 54A-54E illustrate cannula retention mechanisms.
Figure 54B:
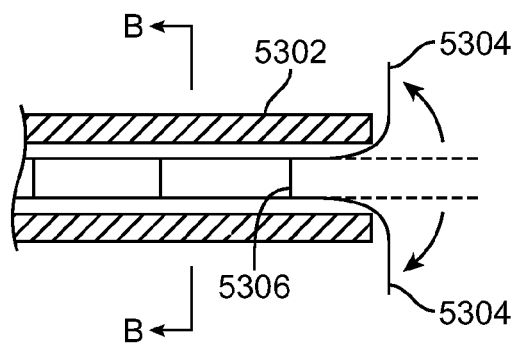
Figure 54C:
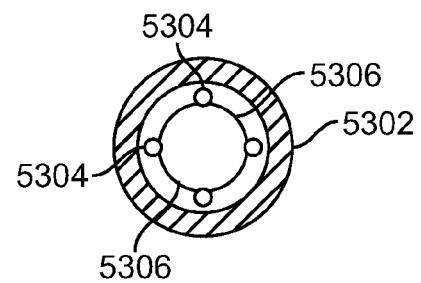

The invention further provides a system comprising an internal distraction catheter and a specialized cannula adapted for introduction of the catheter into the joint capsule. The cannula may include a retention device as illustrated in FIG. 54A. While various types of retention mechanisms are possible, in this embodiment cannula 5302 is a tubular shaft which includes two to four, or more (four in this exemplary embodiment) axial elements 5304 having distal ends which are biased to deflect radially outward at the distal end of the cannula. Thus, once the axial elements are advanced through the cannula and become unconstrained, they deflect outward forming a flanged region which serves as an anchor and prevents the cannula from pulling out and away from the capsule. A distraction device having a balloon 5308 mounted to a shaft 5312 near the distal tip 5310 of the shaft also is inserted into the cannula 5302. The proximal end of shaft 5312 includes a Y-connector 5318 which allows an inflator to be fluidly coupled with the balloon 5308 and another device, such as a syringe for irrigation to be fluidly coupled with the inflation catheter. A shoulder 5314 on the proximal end of the cannula 5302 allows the tube to be manipulated by a surgeon and a shoulder 5316 on the proximal end of the retention device allows the axial elements 5304 to be advanced from and retracted into the cannula. FIG. 54B highlights the distal end of the cannula and retention mechanism. FIG. 54C illustrates a cross section of FIG. 54A taken along line B-B and illustrates that the four axial elements 5304 also may be connected with rings 5306 which help bias the axial elements outward against the inner surface of the cannula to provide maximum space for instruments to be passed therethrough. In the embodiment illustrated axial elements 5304 and rings 5306 are removable from the tubular cannula 5302 although in alternative embodiments the axial elements may be permanently attached to the cannula or integrally formed therewith. The axial elements may be fabricated from a superelastic or shape memory alloy such as nitinol or a spring temper stainless steel or other resilient metal or polymer may be used. Thus, the retention device retains the distal end of the cannula in the joint capsule and allows the cannula to be as short as possible to provide a clear space distally in which to work. In addition, traction may be applied to the cannula to distend the capsular ligaments, thereby increasing the space within the capsule to allow better access and visualization of the joint.

Figure 54D:
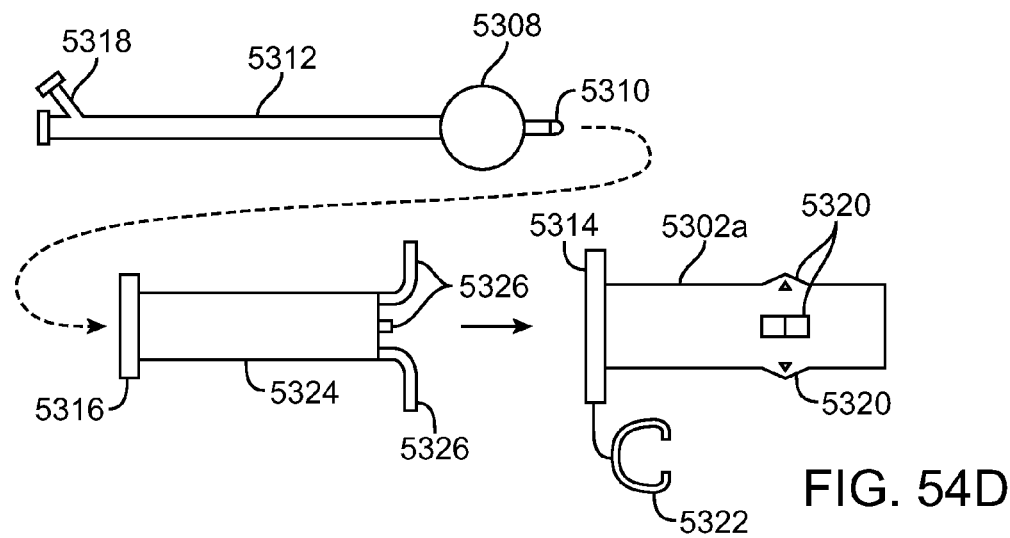
Figure 54E:
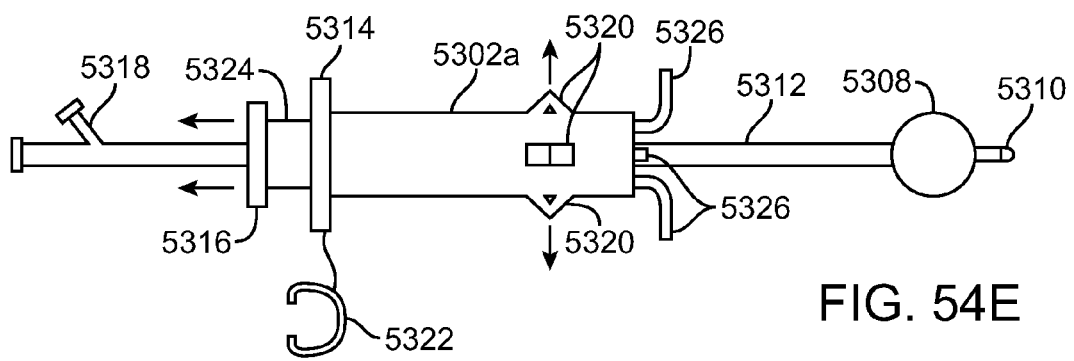

Another embodiment of a system having an internal distraction catheter and a specialized cannula adapted for introduction of the catheter into the joint capsule is illustrated in FIGS. 54D-54E. The system includes a distraction device having a balloon 5308 mounted to a shaft 5312 near the distal end 5310 of the shaft. A Y-connector 5318 or other connector is used to fluidly couple the balloon 5308 with an inflation device and a second device such as a syringe or irrigation device. The cannula 5302a includes four articulated hinges 5320 that deflect radially outward forming wings when the cannula 5302a is axially compressed. A shoulder 5314 on the proximal end of the cannula 5302a allows a surgeon to easily grasp and manipulate the cannula and a C-ring 5322 serves as a locking mechanism as will be described below. An inner sleeve 5324 includes a plurality of wire-like filaments 5326 (here 4 filaments) that are biased to deflect radially outward when unconstrained. A shoulder 5316 on the proximal end of the inner sleeve 5316 allows a surgeon to grasp and manipulate the inner sleeve. In use, the inner sleeve 5324 is advanced into the central channel of cannula 5302a. Filaments 5326 deflect radially inward as the inner sleeve is advanced into the cannula, until the filaments reach the distal end of the cannula and then become unconstrained and flare radially outward as seen in FIG. 54E. The inner sleeve is then retracted proximally to apply a compressive load against cannula 5302a which forces the hinges 5320 to bend and expand radially outward forming wings. Thus, two anchor portions are formed—a proximal anchor portion consisting of the outwardly deflected hinges 5320 and the flared filaments 5326. This configuration may be used to help anchor the cannula to tissue, such as when the filaments are inside the capsule and the hinges are outside the capsule but under the skin. The C-ring 5322 may be snapped around the inner sleeve 5324 between the two shoulders 5316, 5314, thereby maintaining the separation between the two shoulders and thus keeping the hinges 5320 deflected radially outward. The distraction device may then be inserted into the cannula to distract a joint. Once the procedure is completed, the C-ring may be removed from the inner sleeve allowing the hinges to return to their normal flush configuration with the cannula. The inner sleeve may also be retracted into the cannula to remove the filaments and allow the cannula to be withdrawn from the capsule. Embodiments of the cannula with a retention mechanism may also be used when tension on the joint capsule is relaxed (e.g. by flexion of the joint). This allows the cannula to be pulled outwardly away from the joint while the retention features are deployed and helps "tent up" the capsule to provide more space.

Figure 55A:
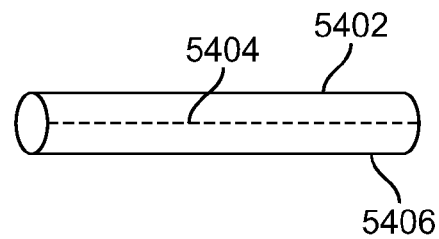
FIGS. 55A-55B, 56 and 57 illustrate various embodiments of cannulas.
Figure 55B:
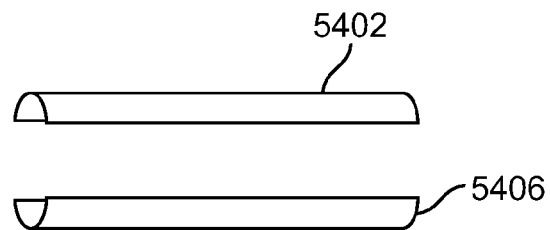
Figure 56:
Figure 57:
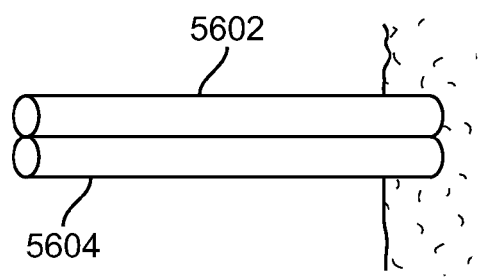

Still other embodiments of cannulas which may be used with the distraction tools disclosed herein include the split cannula seen in FIG. 55A. The cannula includes an upper portion 5402 and a lower portion 5406 that are coupled together with a releasable seam 5404 (e.g. a perforation). Once the cannula has been placed into the joint space and the distraction device or other instruments have been delivered to their target site, the upper portion 5402 may be separated from the lower portion 5406 and one or both portions removed from the patient as seen in FIG. 55B. In still other embodiments, a C-shaped or half pipe shaped cannula 5502 seen in FIG. 56 may be used and in still other embodiments such as in FIG. 57, double barreled cannulas 5602, 5604 may be inserted into a single portal. Each of these embodiments helps introduce more instruments into the joint space using fewer portals or helps more instruments to be introduced through a cannula.

While the above is a complete description of the preferred embodiments of the invention, various alternatives, modifications, and equivalents may be used. The various features of the embodiments disclosed herein may be combined or substituted with one another. Therefore, the above description should not be taken as limiting in scope of the invention which is defined by the appended claims.

What is claimed is:

1. A method for treating a hip joint of a leg, wherein the hip joint comprises a concave acetabular cup surface rotatably supporting a convex femoral head surface, the concave acetabular CUP surface of the hip joint comprises a fossa, said method comprising the steps of:
   providing an elongate member having a proximal end, a distal end and an ex1pandable member near the distal end;
   positioning the expandable member in the joint between the concave acetabular cup surface and the convex femoral head surface, wherein the step of positioning the expandable member in the joint comprises positioning at least a portion of the expandable member in the acetabular fossa;
   expanding the expandable member, while the expandable member remaining in the acetabular fossa during the expansion of the expandable member, so as to displace the convex femoral head surface from the concave acetabular cup surface;
   while the displaced convex femoral head surface is supported on the expanded expandable member, manipulating the displaced convex femoral head surface vis-a-vis the concave acetabular cup surface, wherein such manipulation comprises rotating the displaced convex femoral head surface about the concave acetabular cup surface, and further wherein such manipulation comprises at least one from the group consisting of flexion, extension, lateral rotation, medial rotation, abduction and adduction of the leg; and
   while the displaced and manipulated convex femoral head surface is supported on the expanded expandable member, performing a therapeutic procedure on the joint.

2. The method of claim 1, wherein manipulation comprises flexion of more than 20 degrees.

3. The method of claim 1, further comprising reducing tension in an anterior portion of a capsule surrounding the hip joint.

4. The method of claim 3, wherein performing the therapeutic procedure comprises positioning at least one instrument through the anterior portion of the capsule while tension in the capsule of the joint is reduced.

5. The method of claim 1, wherein manipulation comprises bending the knee ipsilateral to the hip joint being treated.

6. The method of claim 1, further comprising maintaining the hip joint in a manipulated configuration with a brace releasably coupled with the patient's leg ipsilateral to the hip joint being treated.

7. The method of claim 1, wherein the step of positioning comprises advancing the expandable member over a guidewire into the hip joint.

8. The method of claim 1, wherein the step of positioning comprises advancing the expandable member through a cannula extending into a capsule surrounding the hip joint.

9. The method of claim 8, further comprising deploying a retention mechanism from the cannula, the retention mechanism anchoring the cannula in the capsule of the hip joint.

10. The method of claim 1, wherein the step of expanding the expandable member comprises inflating a balloon.

11. The method of claim 10, wherein the balloon is inflated to a pressure not exceeding about 100 psi.

12. The method of claim 10, wherein the balloon exerts at least about 50 pounds of force against the concave acetabular cup surface and the convex femoral head surface.

13. The method of claim 1, wherein the expandable member engages each of the concave acetabular cup surface and the convex femoral head surface within a contact area, the contact area being no more than about 800 mm$^2$.

14. The method of claim 1, wherein each of the concave acetabular cup surface and the convex femoral head surface has a total area, and wherein the expandable member engages each of the concave acetabular cup surface and the convex femoral head surface within a contact area, the contact area being no larger than about 50% of the total area.

15. The method of claim 8, wherein the expandable member has an outer surface with a radius of curvature when expanded, the radius of curvature being about 8-18 mm.

16. The method of claim 1, wherein the acetabular cup surface of the hip joint having a total surface area outside the fossa, wherein the expandable member contact s one of the joint surfaces along a contact area, the contact area being less than about 50% of the total surface area outside the fossa when the expandable member is expanded.

17. The method of claim 1, wherein expanding the expandable member separates the convex femoral head surface from the concave acetabular cup surface by at least about 10 mm.

18. The method of claim 1, wherein the step of manipulating the joint comprises abducting the joint through an angle of about 30 to 80 degrees.

19. The method of claim 1, wherein the step of manipulating the joint comprises adducting the joint through an angle of about 10 to 30 degrees.

20. The method of claim 1, wherein the step of performing the therapeutic procedure comprises at least one of labral repair, debridement, lavage, osteotomy, microfracture, and chondral repair.

21. The method of claim 1, further comprising a step of removing the expandable member from the hip joint.

* * * * *